United States Patent [19]

Heistracher et al.

[11] Patent Number: 5,252,540
[45] Date of Patent: Oct. 12, 1993

[54] SULFONAMIDES

[75] Inventors: Elisabeth Heistracher, Ludwigshafen; Klaus Fischer, Speyer; Horst Mayer, Ludwigshafen; Thomas Saupe, Sandhausen; Gerhard Hamprecht, Weinheim; Klaus Ditrich, Bad Duerkheim; Thomas Kuekenhoehner, Frankenthal; Matthias Gerber, Mutterstadt; Helmut Walter, Obrigheim; Karl-Otto Westphalen, Speyer, all of Fed. Rep. of Germany

[73] Assignee: BASF Aktiengesellschaft, Ludwigshafen, Fed. Rep. of Germany

[21] Appl. No.: 760,156

[22] Filed: Sep. 16, 1991

[30] Foreign Application Priority Data

Sep. 20, 1990 [DE] Fed. Rep. of Germany ....... 4029753

[51] Int. Cl.$^5$ .................. A01N 43/56; C07D 231/14
[52] U.S. Cl. .................. 504/280; 504/282; 548/374.1; 548/371.7; 548/368.1; 548/369.7; 548/365.7; 548/365.4; 548/366.7
[58] Field of Search ............... 548/375, 376, 377, 378; 504/280, 282

[56] References Cited

FOREIGN PATENT DOCUMENTS 0244166 11/1987 European Pat. Off. .
0269141 6/1988 European Pat. Off. .

OTHER PUBLICATIONS

Egg, Chem. Abstracts, vol. 71, No. 21; 101768c (1969).
Arzneimittel-Forschung (Drug Research), vol. 24, Mar. 1974, pp. 363-374, V. H. Plumpe, et al., "Isoxazol-carboxamidoalkyl-Benzolsulfonyl-Harnstof-fe,-Semicarbazide und -Aminopyrimidine Sowie Damit Verwandte Verbindungen und Ihre Blutzuckersenkende Wirkung".
Chemische Berichte, vol. 106, Jan. 1973, pp. 1290-1302, G. Siewert, et al., "Hydroxylierung Von 5-Alkyl-2-(-Benzolsulfonylamino) Pyrimidines und Strukturverwandten Antidiabetika".

Primary Examiner—Johann Richter
Attorney, Agent, or Firm—Oblon, Spivak, McClelland, Maier & Neustadt

[57] ABSTRACT

Sulfonamides of the formula I

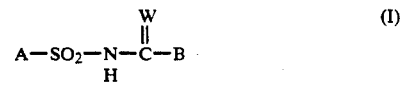

where A is an unsubstituted or substituted aromatic or heteroaromatic radical; W is oxygen or sulfur; B is an unsubstituted or substituted furyl, thienyl, pyrrolyl, oxazolyl, isothiazolyl, imidazolyl, pyrazolyl, thiadiazolyl, oxadiazolyl or triazolyl radical, and the environmentally compatible salts thereof are prepared as described and are used as herbicides.

8 Claims, No Drawings

SULFONAMIDES

The present invention relates to sulfonamides of the formula I

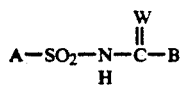

(I)

where A is

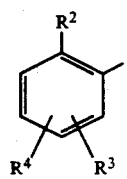
(A1)

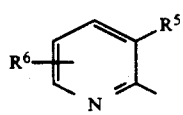
(A2)

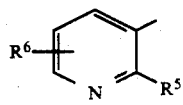
(A3)

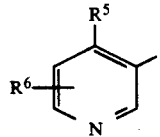
(A4)

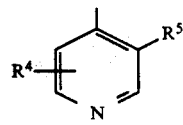
(A5)

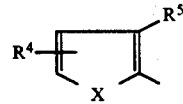
(A6)

(A7)

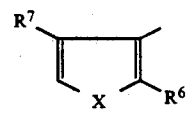
(A8)

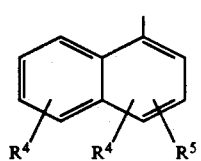
(A9)

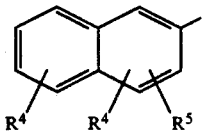
(A10)

W is oxygen or sulfur;

B is 2-, 3-, 4- or 5-furyl, 2-, 3-, 4- or 5-thienyl, each trisubstituted by $R^8$; 2-, 3-, 4- or 5-pyrrol which is trisubstituted on carbon by $R^8$ and monosubstituted on nitrogen by $R^9$; 2-, 4- or 5-oxazolyl, 3-, 4- or 5-isoxazolyl 2-, 4- or 5-thiazolyl or 3-, 4- or 5-isothiazolyl, each disubstituted by $R^8$; 2-, 4- or 5-imidazolyl or 3-, 4- or 5-pyrazolyl, each disubstituted on carbon by $R^8$ and monosubstituted on nitrogen by $R^9$; 1,3,4-thiadiazol-2-yl,-5-yl,1,3,4-oxadiazol-2-yl,-5-yl, 2,4-thiadiazol-3-yl,-5-yl, 1,2,4-oxadiazol-3-yl,-5-yl, 1,2,3-thiadiazol-4-yl,-5-yl, 1,2,3-oxadiazol-4-yl,-5-yl, 1,2,5-thiadiazol-3-yl,-4-yl, 1,2,5-oxadiazol-3-yl,-4-yl, each of which is monosubstituted by $R^8$; 1,2,4-triazol-3-yl, substituted on carbon by $R^{10}$ and on N-1 by $R^{11}$; 1,2,4-triazol-5-yl or 1,2,3-triazol-4-yl or -5-yl, each substituted on carbon by $R^8$ and on N-1 by $R^9$;

X is oxygen, sulfur or $NR^1$;

$R^1$ is hydrogen; $C_1$-$C_6$-alkyl which is unsubstituted or substituted by one to five halogens and or phenyl; $C_2$-$C_4$-alkenyl; phenyl which is unsubstituted or substituted by one to five halogens and/or one to three of the following: $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio, $C_1$-$C_4$-haloalkylthio, nitro or cyano;

$R^2$ is halogen; cyano; thiocyano; $C_1$-$C_6$-alkyl which can be substituted by one to five halogens and/or one of the following: $C_1$-$C_4$-alkoxy, $C_1$-$C_4$-haloalkoxy, $C_1$-$C_4$-alkylthio, $C_1$-$C_4$-haloalkylthio, phenyl, phenoxy or phenylthio, where each of the phenyls can be substituted by one to five halogens and/or one to three of the following: $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio or $C_1$-$C_4$-haloalkylthio; $C_3$-$C_6$-cycloalkyl, $C_3$-$C_8$-cycloalkoxy, $C_3$-$C_6$-cycloalkylthio, $C_5$-$C_6$-cycloalkenyl, $C_5$-$C_8$-cycloalkenyloxy or $C_5614$ $C_6$-cycloalkenylthio, each of which may be substituted by one to five halogens and/or one to three of the following: $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio or $C_1$-$C_4$-haloalkylthio; phenyl, phenoxy, benzyloxy or benzylthio, each of which may be substituted by one to five halogens and/or one to three of the following: cyano, nitro, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio or $C_1$-$C_4$-haloalkylthio; saturated, singly or doubly unsaturated 5-7-membered heterocycle which contains one or two nitrogen, oxygen and/or sulfur atoms and is unsubstituted or substituted by up to two of the following: halogen, cyano, nitro, $C_1$-$C_4$-alkyl, $C_1$-$C_4$-alkoxy, $C_1$-$C_4$-alkylthio, $C_1$-$C_4$-haloalkyl, $C_1$-$C_4$-haloalkoxy or $C_1$-$C_4$-haloalkylthio; $C_1$-$C_4$-alkoxy or $C_1$-$C_4$-alkylthio, $C_2$-$C_6$-alkenyl or $C_2$-$C_6$-alkenyloxy or $C_2$-$C_6$-alkenylthio, $C_2$-$C_6$-alkynyl, $C_2$-$C_6$-alkynyloxy or $C_2$-$C_6$-alkynylthio, where the said alkoxy, alkylthio, alkenyl, alkynyl, alkenyloxy(thio) and alkynyloxy(thio) may be substituted by one to five halogens and/or one of the following: $C_1$-$C_4$-alkoxy, $C_1$-$C_4$-haloalkoxy, $C_1$-$C_4$-alkylthio, $C_1$–$C_4$-haloalkylthio; phenyl, phenoxy, phenylthio, benzyloxy or benzylthio;

$COR^{12}$; $COQR^{13}$; $SO_2NR^{15}R^{16}$; $SO_2OR^{17}$; $OSO_2R^{18}$; $S(O)_nR^{19}$;

$R^3$ is $R^6$; $COQR^{13}$; $SO_2NR^{15}R^{16}$; $SO_2OR^{16}$; $OSO_2R^{16}$; $S(O)_nR^{19}$;

$R^4$ is hydrogen; halogen; cyano; $C_1$–$C_4$-alkyl or $C_1$–$C_4$-alkyl substituted by one to five halogens; $C_1$–$C_4$-alkoxy; $C_1$–$C_4$-haloalkoxy; $C_1$–$C_4$-alkylthio; $C_1$–$C_4$-haloalkylthio;

$R^5$ is hydrogen; nitro or $R^2$;

$R^6$ is hydrogen; halogen; cyano; $C_1$–$C_4$-alkyl, $C_1$–$C_4$-alkyl substituted by one to five halogens and/or one of the following: $C_1$–$C_4$-alkoxy, $C_1$–$C_4$-haloalkoxy, $C_1$–$C_4$-alkylthio, $C_1$–$C_4$-haloalkylthio, OH, SH or cyano; $C_1$–$C_4$-alkoxy, $C_1$–$C_4$-alkylthio, $C_1$–$C_4$-haloalkoxy or $C_1$–$C_4$-haloalkylthio, each of which may be substituted by the following: $C_1$–$C_4$-alkoxy, $C_1$–$C_4$-haloalkoxy, $C_1$–$C_4$-alkylthio or $C_1$–$C_4$-haloalkylthio;

$R^7$ is nitro; or $R^2$;

$R^8$ is hydrogen; nitro;

or $R^2$, or two vicinal $R^2$ together form a $C_3$ chain or a $C_4$–$C_6$ chain in which one methylene can be replaced by oxygen or $C_1$–$C_4$-alkylimino;

$R^9$ is hydrogen;

$C_1$–$C_6$-alkyl which may be substituted by one to five halogens and/or one of the following: $C_1$–$C_4$-alkoxy; $C_1$–$C_4$-haloalkoxy; $C_1$–$C_4$-alkylthio; $C_1$–$C_4$-haloalkylthio, phenyl, phenoxy or phenylthio, it being possible for the cyclic groups to be substituted by one to five halogens and/or one to three of the following: cyano, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio or $C_1$–$C_4$-haloalkylthio; $C_3$–$C_6$-cycloalkyl or $C_5$–$C_6$-cycloalkenyl, each of which may be substituted by one to five halogens and/or one to three of the following: $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio or $C_1$–$C_4$-haloalkylthio; phenyl which may be substituted by one to five halogens and/or one to three of the following: cyano, nitro, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio or $C_1$–$C_4$-haloalkylthio; $C_2$–$C_6$-alkenyl or $C_2$–$C_6$-alkynyl, each of which may be substituted by one to five halogens and/or one of the following: $C_1$–$C_4$-alkoxy, $C_1$–$C_4$-haloalkoxy, $C_1$–$C_4$-alkylthio or $C_1$–$C_4$-haloalkylthio, phenyl, phenoxy, phenylthio, benzyloxy or benzylthio; $COR^{21}$;

$R^{10}$ is phenyl, benzyl, phenoxy, benzyloxy, phenylthio or benzylthio, each of which may be substituted by one to five halogens and/or one to three of the following: cyano, nitro, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio or $C_1$–$C_4$-haloalkylthio;

$R^{11}$ is hydrogen; phenyl or benzyl, each of which may be substituted by one to five halogens and/or one to three of the following: cyano, nitro, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio or $C_1$–$C_4$-haloalkylthio;

$R^{12}$ is $C_1$–$C_4$-alkyl which is unsubstituted or substituted by halogen or methoxy; $C_3$–$C_5$-cycloalkyl which is unsubstituted or substituted by chlorine or fluorine; $C_3$–$C_4$-alkenyl;

Q is oxygen or $NR^{14}$;

$R^{13}$ is hydrogen; $C_1$–$C_6$-alkyl, $C_1$–$C_6$-alkyl, substituted by one to three of the following: halogen, $C_1$–$C_4$-alkoxy, $C_1$–$C_4$-alkylthio, $C_1$–$C_4$-haloalkoxy, $C_1C_4$-alkoxy-$C_1$–$C_2$-alkoxy, $C_3$–$C_6$-cycloalkyl and/or phenyl; $C_3$–$C_6$-cycloalkyl, $C_3$–$C_6$-cycloalkyl which is substituted once to three times by $C_1$–$C_4$-alkyl; $C_3$–$C_6$-alkenyl; $C_3$–$C_6$-alkynyl; phenyl, phenyl substituted by one to five halogens and/or one to three of the following: cyano, nitro, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio or $C_1$–$C_4$-haloalkylthio;

$R^{14}$ is $OR^{20}$; $R^{13}$ or forms together with another $R^{13}$ a $C_4$–$C_6$-alkylene chain in which one methylene can be replaced by oxygen or $C_1$–$C_4$-alkylimino;

$R^{15}$ is $C_1$–$C_4$-alkyl; $C_3C_4$-alkenyl; $C_3$–$C_4$-alkynyl; cyclopropylmethyl; $C_3$–$C_4$-cycloalkyl;

$R^{16}$ is hydrogen; $C_1$–$C_4$-alkyl; $C_3$–$C_4$-alkenyl; or forms together with $R^{15}$ a $C_4$–$C_6$alkylene chain in which one methylene can be replaced by oxygen;

$R^{17}$ is $C_1$–$C_4$-alkyl; $C_1$–$C_4$-haloalkyl;

$R^{18}$ is $C_1$–$C_4$-alkyl; N,N-dimethylamino;

$R^{19}$ is $C_1$–$C_4$-alkyl; $C_1$–$C_4$-haloalkyl; $C_2$–$C_4$-alkoxyalkyl; $C_3$–$C_4$-alkenyl; $C_3$–$C_4$-alkynyl; $C_3$–$C_4$-haloalkenyl; phenyl; phenyl substituted by fluorine, chlorine, bromine, methyl or methoxy;

n is 1 or 2;

$R^{20}$ is hydrogen or $C_1$–$C_4$-alkyl;

$R^{21}$ is $R^{12}$; phenyl or benzyl, each of which may be substituted by one to five halogens and/or one to three of the following: cyano, nitro, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio or $C_1$–$C_4$-haloalkylthio;

and the environmentally compatible salts thereof.

The present invention relates to processes for preparing the novel sulfonamides and to herbicides and bioregulators containing the compounds I and to the use thereof for controlling undesired plant growth.

It has been disclosed that certain sulfonylated 1-carbamoyl-2-pyrazolines have herbicidal and/or growth-regulatory properties (EP-A-269 141). In addition, some sulfonylated bi- or tricyclic carboxamides have herbicidal and growth-regulatory activities (EP-A-244 166).

It is an object of the present invention to find sulfonamides with satisfactory properties as herbicides and/or bioregulators.

We have found that this object is achieved by the sulfonamides I which are defined in the first paragraph and are prepared as described. The present invention also relates to herbicides and agents for controlling plant growth which contain the novel compounds I, and to a process for influencing and controlling plant growth with these compounds.

The compounds of the formula I may contain one or more centers of chirality and then exist as mixtures of diastereomers. The present invention embraces both the pure enantiomers or diastereomers and the mixtures thereof.

The compounds of the formula I are able to form salts in which the hydrogen of the —$SO_2$—NH— group is replaced by an agriculturally suitable cation. These salts are generally of metals, in particular alkali metals or alkaline earth metals, but may be of alkylated ammonium or organic amines. They are preferably prepared in inert solvents such as water, methanol or acetone at 0°–100° C. Examples of bases suitable for preparing the salts according to the invention are alkali metal carbonates such as potassium carbonate, alkali metal and alkaline earth metal hydroxides, alkali metal and alkaline earth metal alcoholates, ammonia or ethanolamine.

The term alkyl in the above definitions in each case means straight-chain or branched alkyl.

Likewise, alkenyl and alkynyl mean straight-chain or branched radicals.

The term halogen means fluorine, chlorine, bromine or iodine.

Preferred compounds of the formula I are those where
A is (A1), (A2), (A7), (A8) or (A9),
W is oxygen
X is sulfur
B is 2-, 4- or 5-oxazolyl, 3-, 4- or 5-isoxazolyl, 2-, 4- or 5-thiazolyl or 3-, 4- or 5-isothiazolyl, each of these being disubstituted by R:;
2-, 4- or 5-imidazolyl or 3-, 4- or 5-pyrazolyl, each of these being disubstituted on carbon by R: and monosubstituted on nitrogen by $R^9$;
$R^4$ is hydrogen, and the environmentally compatible salts thereof.

Particularly preferred compounds of the formula I are those where
A is (A1) and
B is 3-, 4- or 5-pyrazolyl, disubstituted on carbon by $R^8$ and monosubstituted on nitrogen by $R^9$, and the environmentally compatible salts thereof.

The compounds of the formula I can be obtained in a wide variety of ways similar to known reaction methods. Seven processes (A to G) are explained hereinafter by way of example.

PROCESS A

Compounds of the formula I with W=O are obtained in a conventional manner (M. L. Crossley, E. H. Northey, M. E. Hultquist, J. Am. Chem. Soc. 61, (1939), 2950-2955) by reacting an appropriate sulfonamide II in an inert organic solvent in the presence of a base with an acid halide of the formula III as shown below:

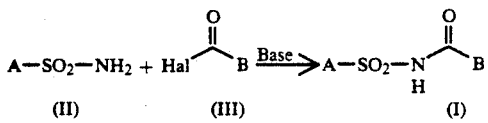

(II)      (III)      (I)

Hal in formula III is chlorine or bromine.

The solvents expediently used for these reactions are halohydrocarbons, e.g. tetrachloromethane, chloroform, methylene chloride, dichloroethane, chlorobenzene and 1,2-dichlorobenzene; ethers, e.g. diethyl ether, methyl tert-butyl ether, dimethoxyethane, diethylene glycol dimethyl ether, tetrahydrofuran and dioxane; ketones, e.g. acetone, ethyl methyl ketone and cyclohexanone; dipolar aprotic solvents, e.g. acetonitrile and N-methylpyrrolidone; aromatic compounds e.g. benzene, toluene, xylene, pyridine, quinoline or mixtures thereof.

The reaction can be carried out at from 0° C. to the reflux temperature of the particular solvent or mixture thereof.

Suitable bases are aromatic nitrogen bases such as pyridine, 4-dimethylaminopyridine or quinoline; tertiary aliphatic amines such as triethylamine, N-ethyl-N,N-diisopropylamine and N-methylmorpholine; bi- and tricyclic amines such as diazabicycloundecene (DBU) or diazabicyclooctane (DABCO) and hydroxides, hydrides, alkoxides, carbonates and bicarbonates of alkali metals and alkaline earth metals, especially sodium hydroxide, potassium hydroxide, sodium hydride, potassium hydride, calcium hydride, lithium hydride, sodium methanolate, sodium ethanolate, potassium tert-butylate, sodium carbonate, potassium carbonate, sodium bicarbonate and potassium bicarbonate. It may also be beneficial to use combinations of the abovementioned bases.

The starting materials II and III are normally employed in the stoichiometric ratio, but an excess of one of the components may be advantageous.

The molar ratio of sulfonamide II to base is generally from 1:1 to 1:3.

The concentration of the precursors in the solvent is generally from 0.1 to 5.0 mol/l, preferably 0.2 to 2.0 mol/l.

It is particularly preferable to use inert aprotic solvents such as methylene chloride, acetone or toluene with sodium hydride, sodium carbonate or potassium carbonate as bases.

PROCESS B

Compounds of the formula I with W=O are obtained in a conventional manner (J. T. Drummond, G. Johnson, Tetrahedron Lett. 29, (1988), 1653-1656) by reacting a compound of the formula IV, in the presence of activating reagents such 2-chloro-1-methylpyridinium iodide, dicyclohexylcarbodiimide or 1,1-carbonyldiimidazole, and in the presence or absence of a base, with a compound of the formula II.

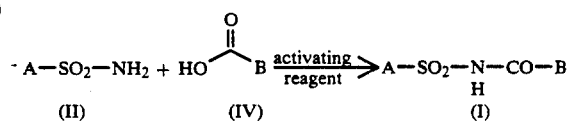

(II)      (IV)      (I)

The activated carboxylic acid is expediently reacted without intermediate isolation with component II in the presence or absence of a base.

The reactions are expediently carried out in solvents such as halohydrocarbons, e.g. chloroform, methylene chloride, dichloroethane, chlorobenzene or 1,2-dichlorobenzene; ethers, e.g. diethyl ether, methyl tert-butyl ether, dimethoxyethane, diethylene glycol dimethyl ether, tetrahydrofuran or dioxane; dipolar aprotic solvents, e.g. acetonitrile; aromatic compounds, e.g. benzene, toluene or xylene or mixture thereof.

The reactions can be carried out at from −30° C. to the reflux temperature of the particular solvent or mixture thereof.

Examples of bases which are used are organic nitrogen bases such as pyridine, 4-dimethylaminopyridine, quinoline, triethylamine, N-ethyl-N,N-diisopropylamine, diazabicycloundecene (DBU) etc., and hydroxides, hydrides, alkoxides, carbonates and bicarbonates of alkali metals and alkaline earth metals, especially sodium hydroxide, potassium hydroxide, sodium hydride, potassium hydride, sodium methanolate, sodium ethanolate, potassium tert-butylate, sodium carbonate, calcium carbonate, potassium carbonate, sodium bicarbonate or potassium bicarbonate. It may also be advantageous to use combinations of the abovementioned bases.

The starting materials II and IV, and the activating reagent, are normally employed in the stoichiometric ratio, but an excess of one of the components may be advantageous.

PROCESS C

Compounds of the formula I with W=O can be obtained in a conventional manner (M. Seefelder, Chem. Ber. 96, (1963), 3243-3253) by reacting a compound of the formula V with a compound of the formula VI

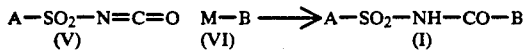

M in formula VI is hydrogen or lithium.

It is expedient to use inert solvents such as halohydrocarbons, e.g. chloroform, methylene chloride, dichloroethane, chlorobenzene or 1,2-dichlorobenzene; ethers, e.g. tetrahydrofuran, dioxane, dimethoxyethane, diethylene glycol dimethyl ether; aromatic compounds, e.g. benzene, toluene, xylene or nitrobenzene, or mixtures thereof.

The reactions can be carried out at from −78° C. to the reflux temperature of the particular solvent or mixture thereof.

The precursors V and VI are normally employed in the stoichiometric ratio, but an excess of one of the components may be advantageous in a few cases.

PROCESS D

Compounds of the formula I with W=O can be obtained in a conventional manner (GB-2 092 136) by reacting a compound of the formula VII with a compound of the formula VIII in the presence of a strong base.

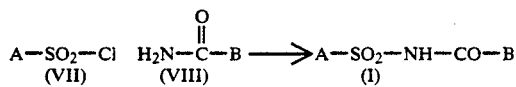

It is expedient to polar, aprotic solvents, e.g. acetonitrile, nitromethane, nitroethane, nitrobenzene, pyridine, benzonitrile, N,N-dimethylformamide, N,N-diethylformamide, N,N-dimethylacetamide, dimethyl sulfoxide, N-methylpyrrolidone, dioxane, tetrahydrofuran, dimethoxyethane, diethylene glycol dimethyl ether or mixtures thereof.

The reactions are usually carried out at from −20° C. to the reflux temperature of the particular solvent or mixture thereof.

The bases normally used are inorganic bases such as oxides, hydroxides, hydrides, carbonates, bicarbonates and alkali metal alkoxides, especially sodium oxide, lithium oxide, potassium oxide, sodium hydroxide, potassium hydroxide, sodium hydride, potassium hydride, calcium hydride, sodium methanolate, sodium ethanolate, potassium tert-butylate, sodium carbonate, potassium carbonate, sodium bicarbonate and potassium bicarbonate. It may also be advantageous to use combinations of the abovementioned bases.

As a rule, the starting materials VII and VIII and the base are employed in the stoichiometric ratio, but an excess of one of the components may be advantageous.

PROCESS E

Compounds of the formula I with W=O are obtained in a conventional manner (M. M. Kremlev, V. G. Dolyuk, J. Org. Chem. (USSR) 10, (1974), 671-672) by reacting a compound of the formula IX and a compound of the formula X with a compound of the formula XI,

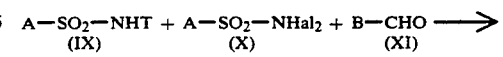

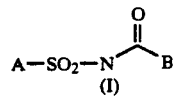

where T is alkali metal and Hal is chlorine or bromine.

It is expedient to use inert solvents such as halohydrocarbons, e.g. chloroform, methylene chloride, dichloroethane, tetrachloromethane, chlorobenzene or 1,2-dichlorobenzene; aromatic compounds, e.g. benzene, toluene, xylene or nitrobenzene or mixtures thereof. The reactions can be carried out at from 0° C. to the reflux temperature of the particular solvent or mixture thereof.

The precursors are normally employed in the stoichiometric ratio, but an excess of one of the components may be advantageous in a few cases.

PROCESS F

Compounds of the formula I with W=S are obtained by processes similar to those disclosed in the literature (S. Scheibye, B. S. Pederson, S. O. Lawesson, Bull. Soc. Chim. Belg. 87, (1978), 229-238) by reacting a compound of the formula I obtained by process A to E with the compound of the formula XII

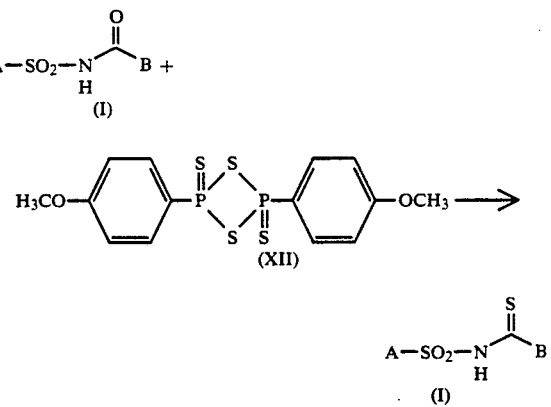

in an inert aprotic solvent such as benzene, toluene, xylene, HMPA, dimethoxyethane or diethylene glycol dimethyl ether or mixtures thereof.

The reaction can be carried out at from about 0° C. to the reflux temperature of the particular solvent or mixture thereof.

The starting materials I (W=O) and XII are normally employed in the stoichiometric ratio, but an excess of one component may be advantageous.

PROCESS G

Compounds of the formula I are obtained by processes known from the literature or similar thereto (T. L. Gilchrist, Heterocyclic Chemistry, Pitman Publisher, London (1985)) by reacting a compound of the formula XIII obtained by process A to E with a nucleophile

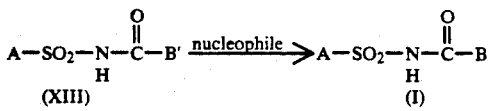

where the heterocycle B' carries a C-bonded substituent which acts as leaving group. This entails the leaving group, such as phenolate, chloride, bromide, etc., being replaced by the nucleophile unit.

Examples of nucleophiles which can be used are alcoholates, thiolates, hydrides and alkali metal alkyls.

It is expedient to use, appropriate for the particular nucleophile, polar aprotic solvents such as dimethyl sulfoxide (DMSO), dimethylformamide (DMF), polar solvents such as alcohols, water, etc., inert solvents such as diethyl ether, methyl tert-butyl ether, tetrahydrofuran (THF), dioxane, dimethoxyethane and diethylene glycol dimethyl ether or mixtures thereof.

The reactions are normally carried out at from $-78°$ C. to the reflux temperature of the particular solvent or mixture thereof.

As a rule, the starting materials are employed in the stoichiometric ratio, but an excess of one of the components may be advantageous.

The sulfonamides of the formula II employed in processes A and B are in many cases commercially available. Novel sulfonamides of the formula II can be prepared by conventional methods (S. Pawlenko in Methoden der organischen Chemie, Houben-Weyl, vol. E 11/II, pages 1098 et seq. 4th edition, Thieme Verlag, Stuttgart 1985).

The acid halides of the formula III used in process A can be prepared in a conventional manner (M. F. Ansell, in The Chemistry of acyl halides (ed. S. Patai), pages 35 et seq., 1st edition, Interscience Publishers, London (1972)) from the corresponding carboxylic acids (IV)

 (IV)

or the salts thereof, with organic acid halides such as oxalyl chloride, phosgene or benzoyl chloride or with inorganic acid halides such as $POHal_3$, $PHal_3$, $PHal_5$, $SOCl_2$, $P(C_6H_5)_3Hal_2$ etc. or binary systems such as $P(C_6H_5)_3/CCl_4$ etc.

It may in some cases be expedient to add a suitable base, especially organic nitrogen bases such as pyridine, 2,6-lutidine or triethylamine, or a suitable catalyst such as dimethylformamide or 4-dimethylaminopyridine.

The carboxylic acids of the formula IV are known from the literature or can be prepared by methods similar to those disclosed in the literature (R. Sustmann, H. G. Korth in Methoden der organischen Chemie, Houben-Weyl, vol. E 5/I, pages 193 et seq., 4th edition, Thieme Verlag, Stuttgart 1985).

The sulfonyl isocyanates of the formula V are prepared by standard processes known to those skilled in the art (Newer Methods of Preparative Organic Chemistry, vol. VI, pages 223 et seq., Academic Press, New York).

The compounds of the formula VI required for process C can likewise be prepared by standard processes.

The sulfonyl chlorides of the formula VII employed for process D are in many cases commercially available. Novel sulfonyl chlorides of the formula VII can be prepared by processes known to those skilled in the art (S. Pawlenko in Methoden der organischen Chemie, Houben-Weyl, vol. E 11/I, pages 1067 et seq., 4th edition, Thieme Verlag, Stuttgart 1985).

Compounds of the formula VIII are known from the literature or can be prepared by known methods (D. Deöpp, H. Döpp in Methoden der organischen Chemie, Houben-Weyl, vol. E 5/II, pages 934 et seq., 4th edition, Thieme Verlag, Stuttgart 1985).

The salts of the formula IX are prepared by standard processes (F. Muth in Methoden der organischen Chemie, Houben-Weyl, vol. 9, pages 629 et seq., 4th edition, Thieme Verlag, Stuttgart 1955).

The halosulfonamides of the formula X are likewise known from the literature or can be prepared in a conventional manner (F. Muth in Methoden der organischen Chemie, Houben-Weyl, vol. 9, pages 641 et seq., 4th edition, Thieme Verlag, Stuttgart 1955).

The aldehydes of the formula XI can be synthesized by known processes (O. Bayer in Methoden der organischen Chemie, Houben-Weyl, vol. 7/1, 4th edition, Thieme Verlag, Stuttgart 1954; vol. E3, 4th edition, Thieme Verlag, Stuttgart 1983).

With a view to the intended use, the preferred compounds of the formula I have substituents with the following meanings:

X is oxygen, sulfur or $NR^1$, $R^1$ is hydrogen; $C_1C_6$-alkyl, especially $C_1$-$C_4$-alkyl such as methyl, ethyl, propyl, 1-methylethyl, butyl, 1-methylpropyl, 2-methylpropyl and 1,1-dimethylethyl, which is unsubstituted or substituted by 1 to 5, in particular 1 to 3, halogens such as fluorine, chlorine or bromine and/or by phenyl. $C_2$-$C_4$-alkenyl, such as ethenyl, 1-propenyl, 2-propenyl, 1-methylethenyl, 1-butenyl, 2-butenyl, 3-butenyl, 1-methyl-1-propenyl, 2-methyl-2-propenyl, 1-methyl-2-propenyl, 2-methyl-1-propenyl, phenyl or phenyl substituted by 1 to 5 halogens such as fluorine, chlorine or bromine and/or one to three of the initially mentioned substituents.

$R^2$ is halogen such as fluorine, chlorine, bromine or iodine, especially fluorine, chlorine and bromine, cyano and thiocyano; $C_1$-$C_6$-alkyl such as methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-methylpropyl and 1-ethyl-2-methylpropyl which is substituted by 1 to 5 halogens, especially fluorine, chlorine or bromine, and/or by one of the following: $C_1$-$C_4$-alkoxy or $C_1$-$C_4$-alkylthio, such as methoxy, ethoxy, propoxy, 1-methylethoxy, butoxy, 1-methylpropoxy, 2-methylpropoxy, 1,1-dimethylethoxy and the corresponding alkylthios, which may be substituted by halogen, especially fluorine, chlorine or bromine, or phenyl, phenoxy, phenylthio, optionally substituted by one to five halogens, especially fluorine, chlorine and bromine and/or one to three $C_1$-$C_4$-alkyl or $C_1$-$C_4$-alkoxy radicals; $C_3$-$C_6$-cycloalkyl and $C_3$-$C_6$-cycloalkylthio, such as cyclopropyl, cyclobutyl, cyclopentyl and cyclohexyl, especially cyclopropyl, cyclopentyl, cyclohexyl, which can carry one to five halogens, especially fluorine, chlorine and bromine, and/or one to three of the following: $C_1-C_4$-alkyl, $C_1-C_4$-haloalkyl, $C_1-C_4$-alkoxy, $C_1-C_4$-haloalkoxy, $C_1-C_4$-alkylthio, $C_1-C_4$-haloalkylthio, especially methyl, and the corresponding cycloalkylthio radicals; $C_3-C_8$-cycloalkoxy such as cyclopropoxy, cyclobutoxy, cyclopentoxy, cyclohexoxy, cycloheptoxy, cyclooctoxy, especially cyclopropoxy, cyclopentoxy and cycloheptoxy, which can be substituted by one to five halogens, especially fluorine, chlorine and bromine, and/or one to three of the following: $C_1-C_4$-alkyl, $C_1-C_4$-haloalkyl, $C_1-C_4$-haloalkoxy, $C_1-C_4$-alkylthio and $C_1-C_4$-haloalkylthio, especially methyl; $C_5-C_6$-cycloalkenyl such as 1-cyclopentenyl, 2-cyclopentenyl, 3-cyclopentenyl, 1-cyclohexenyl, 2-cyclohexenyl or 3-cyzlohexenyl, which can be substituted by one to five halogens, especially fluorine, chlorine or bromine, and/or one to three of the following: $C_1-C_4$-alkyl, $C_1-C_4$-haloalkyl, $C_1-C_4$-alkoxy, $C_1-C_4$-haloalkoxy, $C_1-C_4$-haloalkylthio and $C_1-C_4$-alkylthio especially methyl; $C_5-C_8$-cycloalkenyloxy or $C_5-C_6$-cycloalkenylthio, such as 1-cyclopentenyloxy, 2-cyclopentenyloxy, 3-cyclopentenyloxy, 1-cyclohexenyloxy, 2-cyclohexenyloxy, 3-cyclohexenyloxy, 1-cycloheptenyloxy, 2-cycloheptenyloxy, 3-cycloheptenyloxy, 4-cycloheptenyloxy, 1-cyclooctenyloxy, 2-cyclooctenyloxy, 3-cyclooctenyloxy, 4-cyclooctenyloxy, which can carry one to five of the following: fluorine, chlorine, bromine or iodine, especially fluorine, chlorine or bromine, and/or one to three of the following: $C_1-C_4$-alkyl, $C_1-C_4$-haloalkyl, $C_1-C_4$-alkoxy, $C_1-C_4$-haloalkoxy, $C_1-C_4$-alkylthio or $C_1-C_4$-haloalkylthio, especially methyl; phenyl, phenoxy, benzyloxy or benzylthio, each of which can be substituted by 1 to 5 halogens, especially fluorine, chlorine or bromine, and/or one to three of the following: cyano, nitro, $C_1-C_4$-alkyl, $C_1-C_4$-haloalkyl, $C_1-C_4$-alkoxy, $C_1-C_4$-haloalkoxy, $C_1-C_4$-alkylthio and $C_1-C_4$-haloalkylthio; saturated, singly or doubly unsaturated 5-7-membered heterocycle containing one or two nitrogen, oxygen and/or sulfur atoms, e.g. thiophene, furan, isoxazole, pyrazole, thiazole, oxazole, oxadiazole, thiadiazole, tetrahydrofuran or tetrahydropyran, where the heterocyclic heteroaromatic radicals can be substituted once or twice by the following: halogen such as fluorine, chlorine, bromine or iodine, especially fluorine, chlorine and bromine, cyano, nitro, $C_1-C_4$-alkyl, $C_1-C_4$-alkoxy, $C_1-C_4$-alkylthio, such as methyl, ethyl, propyl, 1-methylethyl, butyl, 1-methylpropyl, 2-methylpropyl or 1,1-dimethylethyl, which can be substituted by one to five halogens, especially fluorine, chlorine and bromine, and the corresponding alkoxy and alkylthio radicals; $C_1-C_4$-alkoxy or alkylthio such as methoxy, ethoxy propoxy, 1-methylethoxy, butoxy, 1-methylpropoxy, 2-methylpropoxy or 1,1-dimethylethoxy, which can be substituted by one to five halogens, especially fluorine, chlorine or bromine, and/or by one of the following: $C_1-C_4$-alkoxy, $C_1-C_4$-haloalkoxy, $C_1-C_4$-alkylthio or $C_1-C_4$-haloalkylthio, and the corresponding alkylthio radicals; $C_3-C_6$-alkenyl, alkenyloxy or alkenylthio such as ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1,-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl, which can be substituted by one to five halogens, especially fluorine, chlorine or bromine, and/or by one of the following: $C_1-C_4$-alkoxy, $C_1-C_4$-haloalkoxy, $C_1-C_4$-alkylthio or $C_1614$ $C_4$-haloalkylthio, and the corresponding alkenyloxy and alkenylthio radicals; $C_2-C_6$-alkynyl, alkynyloxy or alkynylthio, such as ethynyl, 1-propynyl, 2-propynyl, 1-butynyl, 2-butynyl, 3-butynyl, 1-methyl-2-propynyl, 1-pentynyl, 2-pentynyl, 3-pentynyl, 4-pentynyl, 1-methyl-2-butynyl, 1-methyl-3-butynyl, 2-methyl-3-butynyl, 3-methyl-1-butynyl, 1,1-dimethyl-2-propynyl, 1-ethyl-2-propynyl, 1-hexynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-1-pentynyl, 3-methyl-4-pentynyl, 4-methyl-1-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 3,3-dimethyl-1-butynyl, 1-ethyl-2-butynyl, 1-ethyl-3-butynyl, 2-ethyl-3-butynyl and 1-ethyl-1-methyl-2-propynyl, which can be substituted by one to five halogens, especially fluorine, chlorine or bromine, and/or by one of the following: $C_1-C_4$-alkoxy, $C_1-C_4$-haloalkoxy, $C_1-C_4$-alkylthio or $C_1-C_4$-haloalkylthio, and the corresponding alkynyloxy and alkynylthio radicals; $COR^{12}$ such as alkylcarbonyl with $C_1-C_4$-alkyl as mentioned for $R^{12}$, such as cycloalkylcarbonyl with $C_3-C_5$-cycloalkyl as mentioned for $R^{12}$, such as alkenylcarbonyl with $C_3-C_4$-alkenyl as mentioned for $R^{12}$, especially methylcarbonyl, ethylcarbonyl and cyclopropylcarbonyl; $COQR^{13}$ such as carboxyl, such as alkoxycarbonyl with $C_1-C_6$-alkyl as mentioned for $R^{13}$, cycloalkoxycarbonyl with $C_3-C_6$-cycloalkyl as mentioned for $R^{13}$, such as alkenyloxycarbonyl with $C_3-C_6$-alkenyl as mentioned for $R^{13}$ such as alkynyloxycarbonyl with $C_3-C_6$-alkynyl as mentioned for $R^{13}$, such as phenoxycarbonyl with phenyl as mentioned for $R^{13}$, such as carboxamide, such as N-alkylaminocarbonyl with $C_1-C_6$-alkyl as mentioned for $R^{13}$, such as N-cycloalkylaminocarbonyl with $C_3-C_6$-cycloalkyl as mentioned for $R^{13}$, such as N-alkenylaminocarbonyl with $C_3-C_6$-alkenyl as mentioned for $R^{13}$, such as N-alkynylaminocarbonyl with $C_3-C_6$-alkynyl as mentioned for $R^{13}$, such as N-phenylaminocarbonyl with phenyl as mentioned for $R^{13}$, such as N,N-dialkylaminocarbonyl with $C_3$–$C_6$-alkyl as mentioned for $R^{13}$, such as N-alkyl-N-cycloalkylaminocarbonyl with $C_3$–$C_6$-alkyl as mentioned for $R^{13}$ and $C_1$–$C_6$-cycloalkyl as mentioned for $R^{13}$, such as N-alkyl-N-phenylaminocarbonyl with $C_1$–$C_{16}$-alkyl as mentioned for $R^{13}$ and phenyl as mentioned for $R^{13}$, such as N-alkoxyaminocarbonyl with alkoxy as described for $R^{14}$, such as 1-azacycloalkylcarbonyl with 1-azacycloalkyl as described for $R^{14}$, especially methoxycarbonyl, ethoxycarbonyl, isopropoxycarbonyl, N-methylaminocarbonyl, and N,N-dimethylaminocarbonyl; $SO_2NR^{15}R^{16}$ such as N-alkylaminosulfonyl with $C_1$–$C_4$-alkyl as described for $R^{15}$, such as N-alkenylaminosulfonyl with $C_3$–$C_4$-alkenyl as described for $R^{15}$, such as N-alkynylaminosulfonyl with $C_3$–$C_4$-alkynyl as described for $R^{15}$, such as N-cyclopropylmethylaminosulfonyl, such as N-cycloalkylaminosulfonyl with $C_3$–$C_4$-cycloalkyl as described for $R^{15}$, such as N,N-dialkylaminosulfonyl with $C_1$–$C_4$-alkyl as described for $R^{15}$ and with $C_1$–$C_4$-alkyl as described for $R^{16}$, such as N-alkyl-N-alkenylaminosulfonyl with $C_1$–$C_4$-alkyl as described for $R^{15}$ and $C_3$–$C_4$-alkenyl as described for $R^{16}$, such as N-alkyl-N-alkynylaminosulfonyl with $C_1$–$C_4$-alkyl as described for $R^{16}$ and $C_3$–$C_4$-alkynyl as mentioned for $R^{15}$, such as N-alkyl-N-cyclopropylmethylaminosulfonyl with $C_1$–$C_4$-alkyl as described for $R^{16}$, such as N-alkyl-N-cycloalkylaminosulfonyl with $C_1$–$C_4$-alkyl as mentioned for $R^{16}$ and $C_3$–$C_4$-cycloalkyl as described for $R^{15}$, such as 1-azacycloalkylsulfonyl with 1-azacycloalkyl as described for $R^{16}$, especially N,N-dimethylaminosulfonyl and N,N-diethylaminosulfonyl; $SO_2OR^{17}$ such as alkoxysulfonyl with $C_1$–$C_4$-alkyl as described for $R^{17}$, such as haloalkoxysulfonyl with $C_1$–$C_4$-haloalkyl as described for $R^{17}$, especially methoxysulfonyl, ethoxysulfonyl and isopropoxysulfonyl; $OSO_2R^{18}$ such as alkylsulfonyloxy with $C_1$–$C_4$-alkyl as described for $R^{18}$, such as N,N-dimethylsulfonyloxy, especially methylsulfonyloxy and ethylsulfonyloxy; $S(O)_nR^{19}$ such as alkylsulfonyl with $C_1$–$C_4$-alkyl as described for $R^{19}$, such as haloalkylsulfonyl with $C_1$–$C_4$-haloalkyl as described for $R^{19}$, such as alkoxyalkylsulfonyl with $C_2$–$C_4$-alkoxyalkyl as described for $R^{19}$, such as alkenylsulfonyl with $C_3$–$C_4$-alkenyl as mentioned for $R^{19}$, such as alkynylsulfonyl with $C_3$–$C_4$-alkynyl as described for $R^{19}$, such as $C_3$–$C_4$-haloalkenylsulfonyl with $C_3$–$C_4$-haloalkenyl as described for $R^{19}$, such as phenylsulfonyl with phenyl as described for $R^{19}$, such alkylsulfinyl with $C_1$–$C_4$-alkyl as mentioned for $R^{19}$, such as haloalkylsulfinyl with $C_1$–$C_4$-haloalkyl as described for $R^{19}$, such as phenylsulfinyl with phenyl as described for $R^{19}$, especially methylsulfonyl, ethylsulfonyl, isopropylsulfonyl, propylsulfonyl, methylsulfinyl, and ethylsulfinyl.

$R^3$ is $R_6$, especially methyl, ethyl, trifluoromethyl, chloromethyl, methoxymethyl, methylthiomethyl, methoxy, ethoxy, isopropoxy, trifluoromethoxy, difluoromethoxy, chlorodifluoromethoxy, 2,2,2-trifluoroethoxy, 2-chloroethoxy, 2-methoxyethoxy, methylthio and ethylthio; chlorodifluoromethoxy, 2,2,2-trifluoroethoxy, 2-chloroethoxy, 2-methoxyethoxy, methylthio and ethylthio; $COQR^{13}$ such as carboxyl, such as alkoxycarbonyl with $C_1$–$C_6$-alkyl as mentioned for $R^{13}$, cycloalkoxycarbonyl with $C_3$–$C_6$-cycloalkyl as mentioned for $R^{13}$ such as alkenyloxycarbonyl with $C_3$–$C_6$-alkenyl as mentioned for $R^{13}$, such as alkynyloxycarbonyl with $C_3$–$C_6$-alkynyl as mentioned for $R^{13}$, such as phenoxycarbonyl with phenyl as mentioned for $R^{13}$, such as carboxamide, such as N-alkylaminocarbonyl with $C_1$–$C_6$-alkyl as mentioned for $R^{13}$, such as N-cycloalkylaminocarbonyl with $C_3$–$C_6$-cycloalkyl as mentioned for $R^{13}$, such as N-alkenylaminocarbonyl with $C_3$–$C_6$-alkenyl as mentioned for $R^{13}$, such as N-alkynylaminocarbonyl with $C_3$–$C_6$-alkynyl as mentioned for $R^{13}$, such as N-phenylaminocarbonyl with phenyl as mentioned for $R^{13}$, such as N,N-dialkylaminocarbonyl with $C_3$–$C_6$-alkyl as mentioned for $R^{13}$, such as N-alkyl-N-cycloalkylaminocarbonyl with $C_3$–$C_6$-alkyl as mentioned for $R^{13}$ and $C_3$–$C_6$-cycloalkyl as mentioned for $R^{13}$, such as N-alkyl-N-phenylaminocarbonyl with $C_1$–$C_6$-alkyl as mentioned for $R^{13}$ and phenyl as mentioned for $R^{13}$, such as N-alkoxyaminocarbonyl with alkoxy as described for $R^{14}$, such as 1-azacycloalkylcarbonyl with 1-azacycloalkyl as described for $R^{14}$, especially methoxycarbonyl, ethoxycarbonyl, isopropoxycarbonyl, N-methylaminocarbonyl, and N,N-dimethylaminocarbonyl; $SO_2NR^{15}R^{16}$ such as N-alkylaminosulfonyl with $C_1$–$C_4$-alkyl as described for $R^{15}$, such as N-alkenylaminosulfonyl with $C_3$–$C_4$-alkenyl as described for $R^{15}$, such as N-alkynylaminosulfonyl with $C_3$–$C_4$-alkynyl as described for $R^{15}$, such as N-cyclopropylmethylaminosulfonyl, such as N-cycloalkylaminosulfonyl with $C_3$–$C_4$-cycloalkyl as described for $R^{15}$, such as N,N-dialkylaminosulfonyl with $C_1$–$C_4$-alkyl as described for $R^{15}$ and with $C_1$–$C_4$-alkyl as described for $R^{16}$, such as N-alkyl-N-alkenylaminosulfonyl with $C_1$–$C_4$-alkyl as described for $R^{15}$ and $C_3$–$C_4$-alkenyl as described for $R^{16}$, such as N-alkyl-N-alkynylaminosulfonyl with $C_1$–$C_4$-alkyl as described for $R^{16}$ and $C_3$–$C_4$-alkynyl as mentioned for $R^{15}$, such as N-alkyl-N-cyclopropylmethylaminosulfonyl with $C_1$–$C_4$-alkyl as described for $R^{16}$, such as N-alkyl-N-cycloalkylaminosulfonyl with $C_1$–$C_4$-alkyl as mentioned for $R^{16}$ and $C_3$–$C_4$-cycloalkyl as described for $R^{15}$, such as 1-azacycloalkylsulfonyl with 1-azacycloalkyl as described for $R^{16}$, especially N,N-dimethylaminosulfonyl and N,N-diethylaminosulfonyl; $SO_2OR^{17}$ such as alkoxysulfonyl with $C_1$–$C_4$-alkyl as described for $R^{17}$, such as haloalkoxysulfonyl with $C_1$–$C_4$-haloalkyl as described for $R^{17}$, especially methoxysulfonyl, ethoxysulfonyl and isopropoxysulfonyl; $OSO_2R^{18}$ alkylsulfonyloxy with $C_1$–$C_4$-alkyl as described for $R^{18}$, such as N,N-dimethylsulfonyloxy, especially methylsulfonyloxy and ethylsulfonyloxy; $S(O)_nR^{19}$ such as alkylsulfonyl with $C_1$–$C_4$-alkyl as described for $R^{19}$, such as haloalkylsulfonyl with $C_1$–$C_4$-haloalkyl as described for $R^{19}$, such as alkoxyalkylsulfonyl with $C_2$–$C_4$-alkoxyalkyl as described for $R^{19}$, such as alkenylsulfonyl with $C_3$–$C_4$-alkenyl as mentioned for $R^{19}$, such as alkynylsulfonyl with $C_3$–$C_4$-alkynyl as described for $R^{19}$, such as $C_3$–$C_4$-haloalkenylsulfonyl with $C_3$–$C_4$-haloalkenyl as described for $R^{19}$, such as phenylsulfonyl with phenyl as described for $R^{19}$, such alkylsulfinyl with $C_1$–$C_4$-alkyl as mentioned for $R^{19}$, such as haloalkylsulfinyl with $C_1$–$C_4$-haloalkyl as described for $R^{19}$, such as phenylsulfinyl with phenyl as described for $R^{19}$, especially methylsulfonyl, ethylsulfonyl, isopropylsulfonyl, propylsulfonyl, methylsulfinyl, and ethylsulfinyl.

$R^4$ is hydrogen, halogen, especially fluorine, chlorine or bromine, cyano, $C_1$–$C_4$-alkyl, $C_1$–$C_4$-alkoxy or $C_1$–$C_4$-alkylthio, such as methyl, ethyl, propyl, 1-methylethyl, butyl, 1-methylpropyl, 2-methylpropyl or 1,1-dimethylethyl, which can be substituted by one to five halogens, especially fluorine, chlorine or bromine, and the corresponding alkoxy and alkylthio radicals, especially methyl, ethyl, fluoromethyl, difluoromethyl, trifluoromethyl, pentafluoroethyl, methoxy, ethoxy, chloromethoxy, dichloromethoxy, trichloromethoxy, fluoromethoxy, difluoromethoxy, chlorodifluoromethoxy, trifluoromethoxy, dichlorofluoromethoxy, 2-fluoroethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy, pentafluoroethoxy and 2-chloroethoxy;

$R^5$ is hydrogen; nitro or $R^2$, especially fluorine, chlorine, bromine, methyl, ethyl, trifluoromethyl, methoxy, ethoxy, 2-chloroethoxy, 2-methoxyethoxy, trifluoromethoxy, methoxycarbonyl, ethoxycarbonyl, N,N-dimethylaminocarbonyl, methylsulfinyl, ethylsulfinyl, methylsulfonyl, ethylsulfonyl, N-isopropylaminosulfonyl and N,N-dimethylaminosulfonyl;

$R^6$ is hydrogen; halogen such as fluorine, chlorine, bromine or iodine, especially fluorine, chlorine and bromine; cyano; $C_1$–$C_4$-alkyl such as methyl, ethyl, propyl, 1-methylethyl, butyl, 1-methylpropyl, 2-methylpropyl and 1,1-dimethylethyl, which can be substituted by one to five halogens especially fluorine, chlorine or bromine and/or one of the following: hydroxyl, mercapto, cyano, $C_1$–$C_4$-alkoxy, $C_1$–$C_4$-alkylthio, such as methoxy, ethoxy, propoxy, butoxy, 1-methylethoxy, 1-methylpropoxy, 2-methylpropoxy or 1,1-dimethylethoxy, which can be substituted by one to five halogens, especially fluorine, chlorine or bromine, and the corresponding alkylthio radicals, especially methyl, ethyl, trifluoromethyl, chloromethyl, methoxymethyl and methylthiomethyl; $C_1$–$C_4$-alkoxy, $C_1$–$C_4$-alkylthio, such as methoxy, ethoxy, propoxy, butoxy, 1-methylethoxy, 1-methylpropoxy, 2-methylpropoxy or 1,1-dimethylethoxy, which can be substituted by one to five halogens, especially fluorine, chlorine or bromine, and/or by the following: $C_1$–$C_4$-alkoxy, $C_1$–$C_4$-alkylthio, such as methoxy, ethoxy, propoxy, butoxy, 1-methylethoxy, 1-methylpropoxy, 2-methylpropoxy and 1,1-dimethylethoxy, which can be substituted by halogens, especially fluorine, chlorine or bromine, and the corresponding alkylthio radicals, especially methoxy, ethoxy, isopropyloxy, trifluoromethoxy, 2,2,2-trifluoroethoxy, difluoromethoxy, 2-chloroethoxy, 2-methoxyethoxy, methylthio and ethylthio;

$R^7$ is nitro or $R^2$, especially fluorine, chlorine, bromine, methyl, ethyl, chloromethyl, fluoromethyl, difluoromethyl, chlorodifluoromethyl, trifluoromethyl, dichlorofluoromethyl, methoxymethyl, methoxycarbonyl, N,N-dimethylaminocarbonyl and ethoxycarbonyl;

$R^8$ is hydrogen, nitro or $R^2$, especially fluorine, chlorine, bromine, iodine, cyano, nitro, methyl, ethyl, propyl, 1-methylethyl, butyl, 1-methylpropyl, 2-methylpropyl and 1,1-dimethylethyl, fluoromethyl, chloromethyl, bromomethyl, difluoromethyl, trifluoromethyl, trichloromethyl, 2-fluoroethyl, 2-chloroethyl, 2,2-difluoroethyl, 2,2,2-trifluoroethyl, 2,2,2-trichloroethyl, pentafluoroethyl, methoxymethyl, 2-mathoxyethyl, 1-methoxyethyl, 2-methoxy-1-methylethyl, ethoxymethyl, benzyl, cyclopropyl, cyclopentyl, cyclohexyl, phenyl, 2-methylphenyl, 3-methylphenyl, 4-methylphenyl, 2-trifluoromethylphenyl, 3-trifluoromethylphenyl, 4-trifluoromethylphenyl, 2-fluorophenyl, 3-fluorophenyl, 4-fluorophenyl, 2-chlorophenyl, 3-chlorophenyl, 4-chlorophenyl, 2-nitrophenyl, 3-nitrophenyl, 4-nitrophenyl, 2-methoxyphenyl, 3-methoxyphenyl, 4-methoxyphenyl, 2-tetrahydropyranyl, 3-tetrahydropyranyl, 2-tetrahydrofuranyl, 3-tetrahydrofuranyl, 2-thienyl, 3-thienyl, 2-furanyl, 3-furanyl, 1-methyl-3-pyrazolyl, 1-methyl-4-pyrazolyl, 1-methyl-5-pyrazolyl, 1-ethyl-3-pyrazolyl, 1-ethyl-4-pyrazolyl, 1-ethyl-5-pyrazolyl, methoxy, ethoxy, isopropoxy, 2-chloroethoxy, 2-methoxyethoxy, trifluoromethoxy, difluoromethoxy, chlorodifluoromethoxy, 2,2,2-trifluoroethoxy, phenoxy, benzyloxy, methylthio, ethylthio, phenylthio, benzylthio, 2-propenyl, 1-methyl-2-propenyl, 2-methyl-2-propenyl, 2-butenyl, 2-propynyl, 1-methyl-2-propynyl, 2-butynyl, methylcarbonyl, ethylcarbonyl, cyclopropylcarbonyl, chloromethylcarbonyl, bromomethylcarbonyl, fluoromethylcarbonyl, trifluoromethylcarbonyl, methoxymethylcarbonyl, carboxyl, methoxycarbonyl, ethoxycarbonyl, isopropoxycarbonyl, 2,2,2-trifluoroethoxycarbonyl, 2-methoxyethoxycarbonyl, benzyloxycarbonyl, aminocarbonyl, N-methylaminocarbonyl, N,N-dimethylaminocarbonyl, N-ethylaminocarbonyl, N,N-diethylaminocarbonyl, N-isopropylaminocarbonyl, N-benzylaminocarbonyl, N-phenylaminocarbonyl, N-methoxyaminocarbonyl, N-ethoxyaminocarbonyl, N,N-dimethylaminosulfonyl, N-methyl-N-ethylaminosulfonyl, N,N-diethylaminosulfonyl, N-methylaminosulfonyl, N-ethylaminosulfonyl, methoxysulfonyl, ethoxysulfonyl, isopropoxysulfonyl, 2-chloroethoxysulfonyl, 2,2,2-trifluoroethoxysulfonyl, methylsulfonyloxy, ethylsulfonyloxy, isopropylsulfonyloxy, N,N-dimethylaminosulfonyloxy, methylsulfinyl, ethylsulfinyl, isopropylsulfinyl, phenylsulfinyl, methylsulfonyl, ethylsulfonyl, isopropylsulfonyl or propylsulfonyl; or 2 vicinal $R^2$ radicals together form a $C_3$ chain such as propylene or a $C_4$–$C_6$ chain in which one methylene can be replaced by oxygen or $C_1$–$C_4$-alkylamino such as methyl-, ethyl-, propyl- or butylimino;

$R^9$ is hydrogen; unsubstituted or substituted $C_1$–$C_6$-alkyl, especially $C_1$–$C_4$-alkyl, such as methyl, ethyl, propyl, 1-methylethyl, butyl, 1-methylpropyl, 2-methylpropyl and 1,1-dimethylethyl, particularly suitable substituents being the following: fluorine, chlorine, bromine, $C_1$–$C_4$-alkoxy, especially methoxy, ethoxy, or phenyl; $C_3$–$C_6$-cycloalkyl or cycloalkenyl, such as cyclopropyl, cyclobutyl, cyclopentyl, cyclohexyl, 1-cyclopentenyl, 2-cyclopentenyl, 3-cyclopentenyl, 1-cyclohexenyl, 2-cyclohexenyl or 3-cyclohexenyl, each of which can be further substituted, preferably by methyl, ethyl, fluorine, chlorine or trifluromethyl; unsubstituted or substituted phenyl; $C_2$–$C_6$-alkenyl or $C_2$–$C_6$-alkynyl as mentioned for $R^2$, especially vinyl, 2-propenyl and 2-propynyl; $COR^{21}$, especially methylcarbonyl, ethylcarbonyl and phenylcarbonyl;

$R^{10}$ is unsubstituted or substituted phenyl, benzyl, phenoxy, phenylthio, benzyloxy or benzylthio, suitable and preferred substituents being fluorine, chlorine, bromine, methyl, ethyl, trifluoromethyl, methoxy and ethoxy;

$R^{11}$ is hydrogen; unsubstituted or substituted phenyl or benzyl, e.g. 2-substituted or 2,4-disubstituted or 2,6- disubstituted or 2,4,6-trisubstituted phenyl or benzyl, suitable substituents being the following: cyano, nitro, $C_1$–$C_4$-alkyl, $C_1$–$C_4$-haloalkyl, $C_1$–$C_4$-alkoxy, $C_1$–$C_4$-haloalkoxy, $C_1$–$C_4$-haloalkylthio, especially phenyl, 2-chlorophenyl, 2-fluorophenyl, 2-methylphenyl, 2-trifluoromethylphenyl, 2-mathoxyphenyl, 2,4-dichlorophenyl, 2,6-dichlorophenyl, 2,6-difluorophenyl, 2,6-dimethylphenyl, 2-chloro-4-trifluoromethylphenyl and 2,6-dichloro-4-trifluoromethylphenyl;

$R^{12}$ is $C_1$–$C_4$-alkyl such as methyl, ethyl, propyl, 1-methylethyl, butyl, 1-methylpropyl, 2-methylpropyl and 1,1-dimethylethyl, each of which may be substituted by halogen, especially fluorine or chlorine or by methoxy; $C_3$–$C_5$-cycloalkyl such as cyclopropyl, cyclobutyl or cyclopentyl, unsubstituted or substituted by chlorine or fluorine; $C_3$–$C_4$-alkenyl such as 1-propenyl, 2-propenyl, 1-methylethenyl, 1-butenyl, 2-butenyl, 3-butenyl, 1-methyl-1-propenyl, 2-methyl-1-propenyl or 2-methyl-2-propenyl;

Q is oxygen or $NR^{14}$ $R^{13}$ is hydrogen; $C_1$–$C_6$-alkyl, especially $C_1$–$C_4$-alkyl, such as methyl, ethyl, propyl, 1-methylethyl, butyl, 1-methylpropyl, 2-methylpropyl and 1,1-dimethylethyl, substituted alkyl e.g. by halogen, especially fluorine, chlorine or bromine, $C_1$–$C_4$-alkoxy, especially methoxy or ethoxy; unsubstituted or substituted $C_3$–$C_9$-cycloalkyl as mentioned for $R^9$, unsubstituted or substituted by methyl or ethyl; $C_3$–$C_6$-alkenyl such as 2-propenyl, 2-butenyl, 3-butenyl, 1methyl-2-propenyl, 2-methyl-2-propenyl, 2-pentenyl, 3-pentenyl, 4-pentenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-2-propenyl, 1-ethyl-2-propenyl, 2-hexenyl, 3-hexenyl, 4-hexenyl, 5-hexenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1,-dimethyl-3-butenyl, 1,2-dimethyl-2-butenyl, 1,2-dimethyl-3-butenyl, 1,3-dimethyl-2-butenyl, 1,3-dimethyl-3-butenyl, 2,2-dimethyl-3-butenyl, 2,3-dimethyl-2-butenyl, 2,3-dimethyl-3-butenyl, 3,3-dimethyl-2-butenyl, 1-ethyl-2-butenyl, 1-ethyl-3-butenyl, 2-ethyl-2-butenyl, 2-ethyl-3-butenyl, 1,1,2-trimethyl-2-propenyl, 1-ethyl-1-methyl-2-propenyl and 1-ethyl-2-methyl-2-propenyl; $C_3$–$C_6$-alkynyl such as ethynyl, 1-propynyl, 2-propynyl, 1-butynyl, 2-butynyl, 3-butynyl, 1-methyl-2-propynyl, 1-pentynyl, 2-pentynyl, 3-pentynyl, 4-pentynyl, 1-methyl-2-butynyl, 1-methyl-3-butynyl, 2-methyl-3-butynyl, 3-methyl-1-butynyl, 1,1-dimethyl-2-propynyl, 1-ethyl-2-propynyl, 1-hexynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-1-pentynyl, 3-methyl-4-pentynyl, 4-methyl-1-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 3,3-dimethyl-1-butynyl, 1-ethyl-2-butynyl, 1-ethyl-3-butynyl, 2-ethyl-3-butynyl and 1-ethyl-1-methyl-2-propynyl; unsubstituted or substituted phenyl, e.g. by halogen, especially fluorine, chlorine or bromine, $C_1$–$C_4$-alkyl, especially methyl or ethyl, $C_1$–$C_4$-haloalkyl, especially trifluoromethyl, difluoromethyl, chlorodifluoromethyl or trichloromethyl, $C_1$–$C_4$-alkoxy, especially methoxy or ethoxy, $C_1$–$C_4$-haloalkoxy, especially trifluoromethoxy, difluoromethoxy or chlorodifluoromethoxy;

$R^{14}$ is $OR^{20}$, especially methyl or ethyl; $R^{13}$ or forms together with $R^{13}$ a $C_4$–$C_6$-alkylene chain such as butylene, pentylene or hexylene in which one methylene can be replaced by oxygen or $C_1$–$C_4$-alkylamino, e.g. methyl- or ethylimino;

$R^{15}$ is $C_1$–$C_4$-alkyl such as methyl, ethyl, propyl, 1-methylethyl, butyl, 1-methylpropyl, 2-methylpropyl and 1,1-dimethylethyl; $C_3$–$C_4$-alkenyl or alkynyl, e.g. 2-propenyl, 2-butenyl, 3-butenyl, 1-methyl-2-propenyl, 2-methyl-2-propenyl, 2-butynyl, 2-propynyl, 3-butynyl, cyclopropylmethyl, cyclopropyl or cyclobutyl;

$R^{16}$ is hydrogen; $C_1$–$C_4$-alkyl as mentioned for $R^{15}$, $C_3$–$C_4$-alkenyl, e.g. 2-propenyl, 2-butenyl, 3-butenyl, 1-methyl-2-propenyl or 2-methyl-2-propenyl; a $C_4$–$C_6$-alkylene chain in which one methylene can be replaced by oxygen;

$R^{17}$ is $C_1$–$C_4$-alkyl as mentioned for $R^{15}$, $C_1$–$C_4$-haloalkyl, especially $C_1$–$C_2$-haloalkyl, such as chloromethyl, dichloromethyl, trichloromethyl, chlorofluoromethyl, fluoromethyl, difluoromethyl, trifluoromethyl, dichlorofluoromethyl, chlorodifluoromethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl and pentafluoroethyl;

$R^{18}$ is $C_1$–$C_4$-alkyl as mentioned for $R^{15}$ or N,N-dimethylamino;

$R^{19}$ is $C_1$–$C_4$alkyl or haloalkyl as mentioned for $R^{17}$, $C_2$–$C_4$-alkoxyalkyl such as methoxy or ethoxyethyl; $C_3$–$C_4$-alkenyl such as 2-propenyl, 2-butenyl, 3-butenyl, 1-methyl-2-propenyl or 2-methyl-2-propenyl, unsubstituted or substituted by halogen, especially fluorine or chlorine; $C_3$–$C_4$-alkynyl such as 2-propynyl, 2-butynyl or 3-butynyl; phenyl or phenyl substituted by one to three fluorine, chlorine, bromine, methyl or methoxy;

n is 1 or 2

$R^{20}$ is hydrogen or $C_1$–$C_4$-alkyl as mentioned for $R^{15}$;

$R^{21}$ is $R^{12}$, especially methyl, ethyl, trifluoromethyl, difluoromethyl or cyclopropyl; phenyl, benzyl, unsubstituted or substituted by, for example, halogen, especially fluorine, chlorine or bromine, cyano, $C_1$–$C_4$-alkyl, especially methyl or ethyl, $C_1$–$C_4$-alkoxy which is unsubstituted or substituted by halogen, especially methoxy, ethoxy or 2-chloroethoxy.

The herbicidal and growth-regulating compounds I according to the invention and the agents containing them can be applied, for example, in the form of directly sprayable solutions, powders, suspensions, including high percentage aqueous, oily or other suspensions or dispersions, emulsions, oily dispersions, pastes, dusting agents, broadcasting agents or granules by spraying, atomizing, dusting, broadcasting or watering. The application forms depend on the purposes for which they are used; in any event, they should ensure maximum dispersion of the active ingredients according to the invention.

The compounds I are suitable in general for preparing directly sprayable solutions, emulsions, pastes or oily dispersions. Suitable inert additives are mineral oil fractions of medium to high boiling point such as kerosine or diesel oil, also coaltar oils and oils of vegetable or animal origin, aliphatic, cyclic and aromatic hydrocarbons e.g. toluene, xylene, paraffin, tetrahydronaphthalene, alkylated naphthalenes or their derivatives, methanol, ethanol, propanol, butanol, cyclohexanol, cyclohexanone, chlorobenzene, isophorone or highly polar solvents such as N,N-dimethylformamide, dimethyl sulfoxide, N-methylpyrrolidone or water.

Aqueous application forms can be prepared from emulsion concentrates, dispersions, pastes, wettable powders or water-dispersible granules by adding water. To prepare emulsions, pastes or oily dispersions, the substances can be homogenized as such or dissolved in an oil or solvent, using wetting agents, adhesion promoters, dispersants or emulsifiers, in water. However, concentrates which are suitable for dilution with water can also be prepared from active substance, wetting agent, adhesion promoter, dispersant or emulsifier and, possibly, solvent or oil.

Suitable surfactants are the alkali metal, alkaline earth metal and ammonium salts of aromatic sulfonic acids, e.g. lignin-, phenol-, naphthalene- and dibutylnaphthalenesulfonic acid, and of fatty acids, alkyl- and alkylarylsulfonates, alkyl, lauryl ether and fatty alcohol sulfates, and salts of sulfated hexa-, hepta- and octadecanols, and of fatty alcohol glycol ethers, condensation products of sulfonated naphthalene and its derivatives with formaldehyde, condensation products of naphthalene or of naphthalenesulfonic acids with phenol and formaldehyde, polyoxyethylene octylphenol ethers, ethoxylated isooctyl-, octyl- or nonylphenol, alkylphenol and tributylphenyl polyglycol ethers, alkylaryl polyether alcohols, isotridecyl alcohol, fatty alcohol-/ethylene oxide condensates, ethoxylated castor oil, polyoxyethylene alkyl ethers or polyoxypropylene, lauryl alcohol polyglycol ether acetate, sorbitol esters, lignin sulfite waste liquors or methylcellulose.

Powders, dusting and broadcasting agents can be prepared by mixing or milling the active substances together with a solid carrier.

Granules, for example coated, impregnated or homogeneous granules, can be prepared by binding the active ingredients to solid carriers such as mineral earths such as silica gel, silicic acids, silicates, talc, kaolin, limestone, lime, chalk, bole, loess, clay, dolomite, diatomaceous earth, calcium and magnesium sulfate, magnesium oxide, milled plastics, fertilizers such as ammonium sulfate, ammonium phosphate, ammonium nitrate and ureas and vegetable products such as cereal meal, bark meal, wood meal and nutshell meal, cellulose powder or other solid carriers.

The formulations contain from 0.1 to 95% by weight, preferably from 0.5 to 90% by weight, of active ingredient. The active ingredients are employed in a purity of from 90 to 100%, preferably 95% to 100% (according to the NMR spectrum).

The compounds I according to the invention can be formulated as follows, for example:

I. 90 parts by weight of compound No 40 are mixed with 10 parts by weight of N-methyl-α-pyrrolidone to give a solution which is suitable for application in the form of very small droplets.

II. 20 parts by weight of compound No. 40 are dissolved in a mixture composed of 80 parts by weight of xylene, 10 parts by weight of the adduct of 8 to 10 moles of ethylene oxide and 1 mole of oleic acid N-monoethanolamide, 5 parts by weight of calcium dodecylbenzenesulfonate and 5 parts by weight of the adduct of 40 moles of ethylene oxide and 1 mole of castor oil. Dispersing the solution in 100,000 parts by weight of water results in an aqueous dispersion which contains 0.02% by weight of the active ingredient.

III. 20 parts by weight of compound No. 40 are dissolved in a mixture composed of 40 parts by weight of cyclohexanone, 30 parts by weight of isobutanol, 20 parts by weight of the adduct of 7 moles of ethylene oxide and 1 mole of isooctylphenol and 10 parts by weight of the adduct of 40 moles of ethylene oxide and 1 mole of castor oil. Dispersing the solution in 100,000 parts by weight of water results in an aqueous dispersion containing 0.02% by weight of the active ingredient.

IV. 20 parts by weight of active ingredient No. 40 are dissolved in a mixture composed of 25 parts by weight of cyclohexanone, 65 parts by weight of a mineral oil fraction of boiling point 210° to 280° C. and 10 parts by weight of the adduct of 40 moles of ethylene oxide and 1 mole of castor oil. Dispersing the solution in 100,000 parts by weight of water results in an aqueous dispersion containing 0.02% by weight of the active ingredient.

V. 20 parts by weight of active ingredient No. 40 are thoroughly mixed with 3 parts by weight of sodium diisobutylnaphthylene-α-sulfonate, 17 parts by weight of the sodium salt of a ligninsulfonic acid from a sulfite waste liquor and 60 parts by weight of powdered silica gel and milled in a hammer mil. Dispersing the mixture in 20,000 parts by weight of water results in a spray liquor containing 0.1% by weight of the active ingredient.

VI. 3 parts by weight of active ingredient No. 40 are mixed with 97 parts by weight of finely divided kaolin. This results in a dusting agent containing 3% by weight of active ingredient.

VII. 30 parts by weight of active ingredient No. 40 are intimately mixed with a mixture of 92 parts by weight of powdered silica gel and 8 parts by weight of liquid paraffin which has been sprayed on to the surface of this silica gel. This results in a formulation of the active ingredient with good adhesion.

VIII. 20 parts by weight of active ingredient No. 40 are intimately mixed with 2 parts by weight of calcium dodecylbenzosulfonate, 8 parts by weight of fatty alcohol polyglycol ether, 2 parts by weight of the sodium salt of a phenol/urea/formaldehyde condensate and 68 parts by weight of a liquid paraffin.

This results in a stable oily dispersion.

The herbicidal and growth-regulating agents for the active ingredients can be applied in the pre-emergence or post-emergence process. If the active ingredients are less well tolerated by certain crop plants it is possible to employ application techniques in which the herbicides are spray on in such a way that the leaves of the sensitive crop plants are touched as little as possible while the active ingredients reach the leaves of unwanted plants growing thereunder or the uncovered surface of the soil (post-directed, lay-by).

The application rates of active ingredient when used as herbicides depend on the control to be achieved, the season, the target plants and the growth stage and are from 0.001 to 3, preferably 0.01 to 2 kg/ha active substance.

The compounds of the formula I are able to influence virtually all stages of development of a plant in various ways and are therefore employed as plant growth regulators. The variety of effects of the growth regulators depends, in particular, a) on the species and variety of the plant, b) on the time of application relative to the stage of development of the plant and to the season,
c) on the site and method of application (e.g. seed dressing, soil treatment, leaf application or trunk injection for trees)
d) on climatic factors, e.g. temperature, amount of precipitation, also on length of daylight and light intensity
e) on the soil characteristics (including fertilization),
f) on the formulation or application form of the active ingredient and, finally,
g) on the active substance concentrations used.

A few of the range of possible uses of the plant growth regulators of the formula I according to the invention in crop cultivation, in agriculture and horticulture are mentioned hereinafter.

A. The compounds according to the invention can be used to inhibit greatly the vegetative growth of the plants, which is evident, in particular, from a reduction in the height of growth. The treated plants accordingly exhibit stunted growth; there is also seen to be a darker color of the leaves.

It is advantageous in practice to reduce the vigor of grass growth on the edges of roads, hedgerows, canal banks and on grassed areas such as parks, sports grounds and orchards, lawns and airports to reduce the labor and cost of grass cutting.

Also of economic interest is the increase in the resistance to lodging of crops prone to this, such as cereals, corn, sunflowers and soybean. The shortening and strengthening of the stalk caused thereby reduces or eliminates the risk of lodging (bending over) of plants under unfavorable weather conditions before harvest.

Another important use of growth regulators is to reduce the height of growth and to alter the timing of ripening of cotton. This makes possible completely mechanized harvesting of this important crop plant.

The costs of pruning fruit and other trees can be saved by using the growth regulators. In addition, the alternation of fruit trees can be stopped by growth regulators.

Growth regulators can also be used to increase or inhibit the production of lateral branches by the plants. This is of interest when, for example, the production of side shoots (suckers) by tobacco plants is to be inhibited in favor of leaf growth.

Growth regulators can be used, for example, to increase considerably the frost resistance of winter rape. On the one hand, this reduces the height of growth and the development of an excessive (and thus particularly frost-susceptible) leaf or plant mass. On the other hand, the young rape plants are, after sowing and before onset of winter frosts, held back in the vegetative stage of development despite favorable growth conditions. This also eliminates the risk of frost on such plants which are prone to premature breakdown of flowering inhibition and to transition into the generative phase. It is also advantageous for other crops, e.g. winter cereals, to be treated with the compounds according to the invention in the fall and thus be well tillered but not too lush for the start of the winter. It is possible in this way to avert an increased sensitivity to frost and, because of the relatively low leaf and plant mass, attack by various diseases (e.g. fungal disease). The inhibition of vegetative growth additionally makes it possible with many crop plants to plant the soil more densely so that a higher yield per soil area can be achieved.

B. The growth regulators can be used to achieve higher yields both of plants parts and of plant constituents. Thus, for example, it is possible to induce the growth of larger amounts of buds, flowers, leaves, fruit, seed kernels, roots and tubers, to increase the content of sugar in sugar beet, sugar cane and citrus fruit, to raise the protein content in cereals or soybean or to stimulate rubber trees to an increased flow of latex.

In this connection, the compounds of the formula I can bring about increased yields by intervening in the plant metabolism or by promoting or inhibiting vegetative and/or generative growth.

C. Finally, plant growth regulators can be used to achieve both an increase or reduction in the length of stages of development and an increase or reduction in the rate of ripening of the harvested parts of the plants before or after the harvest.

Of economic interest is, for example, the facilitation of harvesting which is made possible by the concentration in time of the fall or reduced adhesion to the tree in the case of citrus fruit, olives or other species and varieties of pomes, drupes and caryopses. The same mechanism, i.e. the promotion of the development of separating tissue between the fruit and the leaf and shoot part of the plant is also essential for well-controlled defoliation of crop plants such as cotton.

D. Furthermore, growth-regulators can be used to reduce the water requirement of plants. This is particularly important for agricultural land which needs very costly artificial irrigation, e.g. in arid or semi-arid areas. Use of the substances according to the invention allows the intensity of irrigation to be reduced and thus improves the economics of farming. Growth regulators have the effect of improving utilization of the available water because, inter alia, the width of opening of the stomata is reduced
a thicker epidermis and cuticula is formed
the spread of roots in the soil is improved and
the microclimate in the crop is beneficially affected by more compact growth.

The growth regulators of the formula I to be used according to the invention can be delivered to the crop plants both as seeds (as seed dressing) and via the soil, i.e. through the roots and, particularly preferably, through the leaf by spraying.

A wide variation in the application rate is possible because they are well tolerated by plants.

In view of the wide variety of application methods, the compounds according to the invention or the agents containing them can be used to eradicate unwanted plants in a large number of crops.

| Crop list: Botanical name | English name |
| --- | --- |
| *Allium cepa* | cooking onion |
| *Ananas comusus* | pineapple |
| *Arachis hypogaea* | peanut |
| *Asparagus officinalis* | asparagus |
| *Beta vulgaris* spp. *altissima* | sugar beet |
| *Beta vulgaris* spp. *rapa* | fodder beet |
| *Brassica napus* var. *napus* | rape |
| *Brassica napus* var. *napobrassica* | cabbage rape |
| *Brassica rapa* var. *silvestris* | turnip rape |
| *Camellia sinensis* | tea plant |
| *Carthamus tinctorius* | safflower |
| *Carya illinoinensis* | pecan nut |
| *Citrus limon* | lemon |
| *Citrus sinensis* | orange |
| *Coffea arabica* (*Coffea canephora*, *Coffea liberica*) | coffee |

-continued

| Crop list: Botanical name | English name |
|---|---|
| *Cucumis sativus* | cucumber |
| *Cynodon dactylon* | Bermuda grass |
| *Daucus carota* | carrot |
| *Elaeis guineensis* | oil palm |
| *Fragaria vesca* | strawberry |
| *Glycine max* | soybean |
| *Gossypium hirsutum* (*Gossypium aboreum, Gossypium herbaceum Gossypium vitifolium*) | cotton |
| *Helianthus annuus* | sunflower |
| *Hevea brasiliensis* | para rubber tree |
| *Hordeum vulgare* | barley |
| *Humulus lupulus* | hops |
| *Ipomoea batatas* | sweet potato |
| *Juglans regia* | walnut |
| *Lens culinaris* | lentil |
| *Linum usitatissimum* | flax |
| *Lycopersicon lycopersicum* | tomato |
| *Malus* spp. | apple |
| *Manihot esculenta* | cassava |
| *Medicago sativa* | alfalfa |
| *Musa* spp. | bananas |
| *Nicotiana tabacum* (*N. rustica*) | tobacco |
| *Olea europaea* | olive |
| *Oryza sativa* | rice |
| *Phaseolus lunatus* | lima bean |
| *Phaseolus vulgaris* | bush bean |
| *Picea abies* | spruce |
| *Pinus* spp. | pine |
| *Pisum sativum* | garden pea |
| *Prunus avium* | sweet cherry |
| *Prunus persica* | peach |
| *Pyrus communis* | pear |
| *Ribes sylvestre* | redcurrant |
| *Ricinus communis* | castor bean |
| *Saccharum officinarum* | sugar cane |
| *Secale cereale* | rye |
| *Solanum tuberosum* | potato |
| *Sorghum bicolor* (*S. vulgare*) | millet |
| *Theobroma cacao* | cocoa |
| *Trifolium pratense* | red clover |
| *Triticum aestivum* | wheat |
| *Triticum durum* | durum wheat |
| *Vicia faba* | horse bean |
| *Vitis vinifera* | grape vine |
| *Zea mays* | corn |

To extend the spectrum of action and to achieve synergistic effects, the compounds I according to the invention can be mixed and applied together with numerous representatives of other groups of herbicides or growth regulators. Examples of suitable mixing partners are diazine, 4H-3,1-benzoxazine derivatives, benzothiadiazinones, 2,6-dinitroanilines, N-phenylcarbamates, thiolcarbamates, halo carboxylic acids, triazines, amides, ureas, diphenyl ethers, triazinones, uracils, benzofuran derivatives, cyclohexane-1,3-dione derivatives, quinolinecarboxylic acid derivatives, sulfonylurea derivatives, aryloxy- and heteroaryloxyphenoxypropionic acids and the salts, esters and amides thereof, and others.

It may also be beneficial to apply the compounds I, alone or combined with other herbicides, mixed together with other crop protection agents, for example with pesticides, fungicides or bactericides. Also of interest is the possibility of mixing with mineral salt solutions which are employed to eliminate deficiencies in nutrients or trace elements. It is also possible to add nonphytotoxic oils and oil concentrates.

The examples which follow describe examples of the preparation of the compounds according to the invention.

EXAMPLE 1

N-(2-Methoxycarbonylphenylsulfonyl)-1,5-dimethylpyrazole-3-carboxamide 10.8 g of 2-methoxycarbonylphenylsulfonamide, 8.6 g of 1,5-dimethylpyrazole-3-carbonyl chloride and 13.8 g of potassium carbonate in 200 ml of absolute acetone are refluxed for 8 h. The solvent is removed by distillation and then the residue is taken up in water and the pH is adjusted to 2. The precipitate is filtered off with suction and washed with $H_2O$ until neutral. The residue is stirred with ether, filtered off with suction and dried under reduced pressure. 11.6 g of N-(2-methoxycarbonylphenylsulfonyl)-1,5-dimethylpyrazole-3-carboxamide with a melting point of 176°–177° C. are obtained (active ingredient Example No. 40).

EXAMPLE 2

N-(2-Thienylsulfonyl)-1-methylpyrazole-4-carboxamide 3.8 g of 1-methylpyrazole-4-carboxylic acid and 4.9 g of carbonyldiimidazole in 100 ml of 1,2-dichloroethane are heated at 55° C. for 3.5 h. 4.9 g of 2-thienylsulfonamide and 5.4 ml of triethylamine are added and then the mixture is heated at 55° C. for 13 h. After cooling, 40 ml of 10% strength aqueous NaOH solution are added and then the pH of the aqueous phase is adjusted to 1. The precipitate is removed and dried under reduced pressure. 5.2 g of N-(2-thienylsulfonyl)-1-methylpyrazole-4-carboxamide with a melting point of 174°–180° C. are obtained (active ingredient Example No. 103).

EXAMPLE 3

N-(2-Chlorophenylsulfonyl)-1,4-dimethylimidazole-2-carboxamide 2.0 g of 1,4-dimethylimidazole and 4.3 g of 2-chlorophenylsulfonyl isocyanate in 200 ml of toluene are refluxed for 6 h. The precipitate which forms on cooling is filtered off with suction and washed with acetone. The residue is suspended in acetonitrile/methanol and refluxed for 0.5 h. After cooling, the solid is filtered off with suction and dried under reduced pressure. 2.3 g of N-(2-chlorophenylsulfonyl)-1,4-dimethylimidazole-2-carboxamide with a melting point of 230°–231° C. are obtained. (Active ingredient Example No. 113).

EXAMPLE 4

N-(2,6-Dichlorophenylsulfonyl)-2-methoxythiazole-4-carboxamide 2.3 g of N-(2,6-dichlorophenylsulfonyl)-2-bromothiazole-4-carboxamide and 1.6 g of sodium methanolate in 45 ml of methanol are refluxed for 12 h. After cooling, the precipitate is filtered off with suction, washed with methanol and then dried under reduced pressure. 1.8 g of N-(2,6-dichlorophenylsulfonyl)-2-methoxythiazole-4-carboxamide with a melting point of 162°–165° C. are obtained. (Active ingredient Example No. 34).

The compounds which are listed in Table 1 which follows and in which the substituents A are as follows can be obtained correspondingly by appropriate choice of the starting materials and adjustment of the process conditions.

A1-1:   $R^2 = CO_2CH_3$       $R^3, R^4 = H$

| | | | |
|---|---|---|---|
| A1-2: | $R^2 = CO_2CH_2CH_3$ | $R^3, R^4 = H$ | |
| A1-3: | $R^2 = CO_2CH(CH_3)_2$ | $R^3, R^4 = H$ | |
| A1-4: | $R^2 = CO_2CH_3$ | $R^3 = 6\text{-Cl}$, | $R^4 = H$ |
| A1-5: | $R^2 = CO_2CH_3$ | $R^3 = 6\text{-OCH}_3$, | $R^4 = H$ |
| A1-6: | $R^2 = CO_2CH_3$ | $R^3 = 6\text{-CH}_3$, | $R^4 = H$ |
| A1-7: | $R^2 = CO_2CH_3$ | $R^3 = 6\text{-F}$, | $R^4 = H$ |
| A1-8: | $R^2 = CO_2CH_3$ | $R^3 = 3\text{-Cl}$, | $R^4 = H$ |
| A1-9: | $R^2 = CO_2CH_3$ | $R^3 = 3\text{-F}$, | $R^4 = H$ |
| A1-10: | $R^2 = CO_2CH_3$ | $R^3 = 4\text{-Cl}$, | $R^4 = H$ |
| A1-11: | $R^2 = CO_2CH_3$ | $R^3 = 5\text{-Cl}$, | $R^4 = H$ |
| A1-12: | $R^2 = CO_2CH_3$ | $R^3 = 5\text{-F}$, | $R^4 = H$ |
| A1-13: | $R^2 = CO_2CH_3$ | $R^3 = 5\text{-OCH}_3$, | $R^4 = H$ |
| A1-14: | $R^2 = CO_2CH_3$ | $R^3 = 5\text{-OCHF}_2$, | $R^4 = H$ |
| A1-15: | $R^2 = CON(CH_3)_2$ | $R^3, R^4 = H$ | |
| A1-16: | $R^2 = CON(CH_3)_2$ | $R^3 = 3\text{-Cl}$ | $R^4 = H$ |
| A1-17: | $R^2 = CON(CH_3)_2$ | $R^3 = 3\text{-F}$ | $R^4 = H$ |
| A1-18: | $R^2 = CH_3$ | $R^3 = H$, | $R^4 = H$ |
| A1-19: | $R^2 = CH_2Cl$ | $R^3, R^4 = H$ | |
| A1-20: | $R^2 = CH_2OCH_3$ | $R^3, R^4 = H$ | |
| A1-21: | $R^2 = CH_2SCH_3$ | $R^3, R^4 = H$ | |
| A1-22: | $R^2 = CF_3$ | $R^3, R^4 = H$ | |
| A1-23: | $R^2 = CH_3$ | $R^3 = 5\text{-Cl}$, | $R^4 = H$ |
| A1-24: | $R^2 = CH_3$ | $R^3 = 5\text{-CH}_3$, | $R^4 = H$ |
| A1-25: | $R^2 = CH_3$ | $R^3 = 5\text{-OCH}_3$, | $R^4 = H$ |
| A1-26: | $R^2 = F$ | $R^3, R^4 = H$ | |
| A1-27: | $R^2 = F$ | $R^3 = 6\text{-F}$, | $R^4 = H$ |
| A1-28: | $R^2 = Cl$ | $R^3, R^4 = H$ | |
| A1-29: | $R^2 = Cl$ | $R^3 = 6\text{-Cl}$, | $R^4 = H$ |
| A1-30: | $R^2 = Cl$ | $R^3 = 6\text{-CH}_3$, | $R^4 = H$ |
| A1-31: | $R^2 = Cl$ | $R^3 = 6\text{-OCH}_3$, | $R^4 = H$ |
| A1-32: | $R^2 = Cl$ | $R^3 = 5\text{-CO}_2CH_3$, | $R^4 = H$ |
| A1-33: | $R^2 = Cl$ | $R^3 = 5\text{-Cl}$, | $R^4 = H$ |
| A1-34: | $R^2 = Cl$ | $R^3 = 3\text{-Cl}$, | $R^4 = H$ |
| A1-35: | $R^2 = Cl$ | $R^3 = 6\text{-Cl}$, | $R^4 = 5\text{-Cl}$ |
| A1-36: | $R^2 = Cl$ | $R^3 = 6\text{-Cl}$, | $R^4 = 4\text{-Cl}$ |
| A1-37: | $R^2 = Br$ | $R^3, R^4 = H$ | |
| A1-38: | $R^2 = Br$ | $R^3 = 6\text{-Br}$, | $R^4 = H$ |
| A1-39: | $R^2 = CN$ | $R^3, R^4 = H$ | |
| A1-40: | $R^2 = OCH_3$ | $R^3, R^4 = H$ | |
| A1-41: | $R^2 = OCH_2CH_3$ | $R^3, R^4 = H$ | |
| A1-42: | $R^2 = OCH(CH_3)_2$ | $R^3, R^4 = H$ | |
| A1-43: | $R^2 = OCH_2CH_2Cl$ | $R^3, R^4 = H$ | |
| A1-44: | $R^2 = CH_2CH_2OCH_3$ | $R^3, R^4 = H$ | |
| A1-45: | $R^2 = OCH_2CF_3$ | $R^3, R^4 = H$ | |
| A1-46: | $R^2 = OCF_3$ | $R^3, R^4 = H$ | |
| A1-47: | $R^2 = OCF_2H$ | $R^3, R^4 = H$ | |
| A1-48: | $R^2 = OCH_3$ | $R^3 = 5\text{-Br}$, | $R^4 = H$ |
| A1-49: | $R^2 = OCH_3$ | $R^3 = 5\text{-OCH}_3$, | $R^4 = H$ |
| A1-50: | $R^2 = OCH_2CF_3$ | $R^3 = 5\text{-OCH}_2CF_3$, | $R^4 = H$ |
| A1-51: | $R^2 = SCH_3$ | $R^3, R^4 = H$ | |
| A1-52: | $R^2 = SCH_2CH_3$ | $R^3, R^4 = H$ | |
| A1-53: | $R^2 = SO_2CH_3$ | $R^3, R^4 = H$ | |
| A1-54: | $R^2 = SO_2CH_2CH_3$ | $R^3, R^4 = H$ | |
| A1-55: | $R^2 = SO_2CH_2CH_2CH_3$ | $R^3, R^4 = H$ | |
| A1-56: | $R^2 = SO_2CH(CH_3)_2$ | $R^3, R^4 = H$ | |
| A1-57: | $R^2 = SO_2N(CH_3)_2$ | $R^3, R^4 = H$ | |
| A1-58: | $R^2 = OSO_2CH_3$ | $R^3, R^4 = H$ | |
| A1-59: | $R^2 = OSO_2CH_2CH_3$ | $R^3, R^4 = H$ | |
| A1-60: | $R^2 = COCH_3$ | $R^3, R^4 = H$ | |
| A1-61: | $R^2 = $ phenyl | $R^3, R^4 = H$ | |

| | | |
|---|---|---|
| A2-1: | $R^5 = H$ | $R^6 = H$ |
| A2-2: | $R^5 = CO_2CH_3$ | $R^6 = H$ |
| A2-3: | $R^5 = CO_2CH_2CH_3$ | $R^6 = H$ |
| A2-4: | $R^5 = CON(CH_3)_2$ | $R^6 = H$ |
| A2-5: | $R^5 = Cl$ | $R^6 = H$ |
| A2-6: | $R^5 = CF_3$ | $R^6 = H$ |
| A2-7: | $R^5 = OCH_2CH_3$ | $R^6 = H$ |
| A2-8: | $R^5 = SO_2CH_3$ | $R^6 = H$ |
| A2-9: | $R^5 = SO_2CH_2CH_3$ | $R^6 = H$ |
| A3-1: | $R^5 = H$ | $R^6 = H$ |
| A3-2: | $R^5 = CON(CH_3)_2$ | $R^6 = H$ |
| A6-1: | $R^5 = H$ | $R^4 = H$ | X = S |
| A6-2: | $R^5 = Cl$ | $R^4 = H$ | X = S |
| A6-3: | $R^5 = H$ | $R^4 = 4\text{-Cl}$ | X = S |
| A6-4: | $R^5 = H$ | $R^4 = 5\text{-Cl}$ | X = S |
| A6-5: | $R^5 = CO_2CH_3$ | $R^4 = H$ | X = S |
| A7-1: | $R^6 = H$ | $R^7 = CO_2CH_3$ | X = S |
| A7-2: | $R^6 = H$ | $R^7 = CON(CH_3)_2$ | X = S |
| A8-1: | $R^6 = H$ | $R^7 = CO_2CH_3$ | X = S |
| A9-1: | $R^5 = H$ | $R^4 = H$ | |
| A9-2: | $R^5 = 2\text{-CO}_2CH_3$ | $R^4 = H$ | |
| A9-3: | $R^5 = 2\text{-Cl}$ | $R^4 = H$ | |
| A9-4: | $R^5 = 8\text{-CO}_2CH_3$ | $R^4 = H$ | |
| A9-5: | $R^5 = 8\text{-Cl}$ | $R^4 = H$ | |
| A9-6: | $R^5 = 8\text{-OCH}_3$ | $R^4 = H$ | |
| A9-7: | $R^5 = 8\text{-OCH}_2CH_2OCH_3$ | $R^4 = H$ | |
| A9-8: | $R^5 = 8\text{-OCH}_2Cl$ | $R^4 = H$ | |
| A10-1: | $R^5 = H$ | $R^4 = H$ | |
| A10-2: | $R^5 = 1\text{-CO}_2CH_3$ | $R^4 = H$ | |
| A10-3: | $R^5 = 1\text{-Cl}$ | $R^4 = H$ | |
| A10-4: | $R^5 = 1\text{-OCH}_2CH_2OCH_3$ | $R^4 = H$ | |
| A10-5: | $R^5 = 1\text{-OCH}_2Cl$ | $R^4 = H$ | |

TABLE 1

$$A-SO_2-N-\overset{\overset{O}{\|}}{C}-B$$
$$\phantom{A-SO_2-N}H$$

| No. | A | B | M.p. (°C.) |
|---|---|---|---|
| 1 | A1-1 | 2-furyl | |
| 2 | A1-26 | 2-furyl | 158–160 |
| 3 | A1-29 | 2-furyl | |
| 4 | A1-1 | 2,5-dimethyl-3-furyl | 148–150 |
| 5 | A1-11 | 2,5-dimethyl-3-furyl | |
| 6 | A1-1 | 5-nitro-2-furyl | |
| 7 | A6-1 | 5-nitro-2-furyl | |
| 8 | A1-40 | 5-chloro-2-thienyl | 175–177 |
| 9 | A1-1 | 5-chloro-2-thienyl | |
| 10 | A1-1 | 5-methyl-2-thienyl | 180–181 |
| 11 | A1-18 | 5-methyl-2-thienyl | |
| 12 | A1-1 | 2-pyrrolyl | 220 |
| 13 | A1-29 | 2-pyrrolyl | 210 |
| 14 | A1-1 | 1-methyl-2-pyrrolyl | 162–164 |
| 15 | A1-28 | 1-methyl-2-pyrrolyl | |
| 16 | A1-1 | 3-isoxazolyl | |
| 17 | A1-26 | 3-isoxazolyl | 170–171 |
| 18 | A1-29 | 5-methyl-3-isoxazolyl | 138 |
| 19 | A1-1 | 5-methyl-3-isoxazolyl | |
| 20 | A1-1 | 5-chloromethyl-3-isoxazolyl | |
| 21 | A1-40 | 5-chloromethyl-3-isoxazolyl | |
| 22 | A1-30 | 5-phenyl-3-isoxazolyl | 200–202 |
| 23 | A1-1 | 3-methyl-4-isoxazolyl | 142–143 |
| 24 | A1-1 | 3,5-dimethyl-4-isoxazolyl | |
| 25 | A1-28 | 3,5-dimethyl-4-isoxazolyl | |
| 26 | A1-1 | 5-isoxazolyl | |
| 27 | A1-27 | 5-isoxazolyl | |
| 28 | A1-1 | 3-methyl-5-isoxazolyl | 123–127 |
| 29 | A1-30 | 3-methyl-5-isoxazolyl | 137–139 |
| 30 | A1-1 | 2-bromo-4-thiazolyl | |
| 31 | A1-29 | 2-bromo-4-thiazolyl | >230 |
| 32 | A1-30 | 2-bromo-4-thiazolyl | 151 |
| 33 | A1-1 | 2-methoxy-4-thiazolyl | |
| 34 | A1-29 | 2-methoxy-4-thiazolyl | 162–165 |
| 35 | A1-30 | 2-methoxy-4-thiazolyl | 138 |
| 36 | A1-1 | 2-methyl-4-thiazolyl | |
| 37 | A1-29 | 2-methyl-4-thiazolyl | |
| 38 | A1-1 | 4-methyl-2-thiazolyl | |
| 39 | A1-30 | 4-methyl-2-thiazolyl | |
| 40 | A1-1 | 1,5-dimethyl-3-pyrazolyl | 176–177 |
| 41 | A1-29 | 1,5-dimethyl-3-pyrazolyl | 135–138 |
| 42 | A1-30 | 1,5-dimethyl-3-pyrazolyl | 123 |
| 43 | A1-28 | 1,5-dimethyl-3-pyrazolyl | 89–91 |
| 44 | A1-40 | 1,4-dimethyl-3-pyrazolyl | 123 |
| 45 | A1-18 | 1,5-dimethyl-3-pyrazolyl | 144–145 |
| 46 | A1-27 | 1,5-dimethyl-3-pyrazolyl | 145–147 |
| 47 | A1-33 | 1,5-dimethyl-3-pyrazolyl | 172–178 |
| 48 | A1-11 | 1,5-dimethyl-3-pyrazolyl | 172–174 |
| 49 | A1-10 | 1,5-dimethyl-3-pyrazolyl | 166–169 |
| 50 | A1-9 | 1,5-dimethyl-3-pyrazolyl | 168–169 |
| 51 | A1-2 | 1,5-dimethyl-3-pyrazolyl | 124–125 |
| 52 | A1-3 | 1,5-dimethyl-3-pyrazolyl | |
| 53 | A1-15 | 1,5-dimethyl-3-pyrazolyl | 201–203 |

TABLE 1-continued $$A-SO_2-N(H)-C(=O)-B$$

| No. | A | B | M.p. (°C.) |
|---|---|---|---|
| 54 | A2-9 | 1,5-dimethyl-3-pyrazolyl | 185–188 |
| 55 | A7-1 | 1,5-dimethyl-3-pyrazolyl | 140–142 |
| 56 | A9-1 | 1,5-dimethyl-3-pyrazolyl | 125–128 |
| 57 | A1-1 | 4-bromo-1,5-dimethyl-3-pyrazolyl | 204–205 |
| 58 | A1-28 | 4-bromo-1,5-dimethyl-3-pyrazolyl | 200–201 |
| 59 | A1-26 | 4-bromo-1,5-dimethyl-3-pyrazolyl | 194–195 |
| 60 | A1-30 | 4-bromo-1,5-dimethyl-3-pyrazolyl | 205–206 |
| 61 | A1-29 | 4-bromo-1,5-dimethyl-3-pyrazolyl | 210 |
| 62 | A1-27 | 4-bromo-1,5-dimethyl-3-pyrazolyl | 192–193 |
| 63 | A1-9 | 4-bromo-1,5-dimethyl-3-pyrazolyl | 192–193 |
| 64 | A1-2 | 4-bromo-1,5-dimethyl-3-pyrazolyl | 180–182 |
| 65 | A1-3 | 4-bromo-1,5-dimethyl-3-pyrazolyl | |
| 66 | A2-9 | 4-bromo-1,5-dimethyl-3-pyrazolyl | |
| 67 | A1-1 | 4-chloro-1,5-dimethyl-3-pyrazolyl | 192–194 |
| 68 | A1-11 | 4-chloro-1,5-dimethyl-3-pyrazolyl | 196–197 |
| 69 | A1-29 | 4-chloro-1,5-dimethyl-3-pyrazolyl | 210 |
| 70 | A1-30 | 4-chloro-1,5-dimethyl-3-pyrazolyl | 194–195 |
| 71 | A1-40 | 4-chloro-1,5-dimethyl-3-pyrazolyl | 201–204 |
| 72 | A1-1 | 1,4-dimethyl-3-pyrazolyl | |
| 73 | A1-2 | 1,4-dimethyl-3-pyrazolyl | |
| 74 | A1-28 | 1,4-dimethyl-3-pyrazolyl | |
| 75 | A1-27 | 1,4-dimethyl-3-pyrazolyl | |
| 76 | A1-30 | 1,4-dimethyl-3-pyrazolyl | |
| 77 | A1-1 | 1,4,5-trimethyl-3-pyrazolyl | 184–186 |
| 78 | A1-29 | 1,4,5-trimethyl-3-pyrazolyl | 145–146 |
| 79 | A1-40 | 1,4,5-trimethyl-3-pyrazolyl | |
| 80 | A1-1 | 4-ethoxycarbonyl-1-methyl-3-pyrazoyl | 162–164 |
| 81 | A1-30 | 4-ethoxycarbonyl-1-methyl-3-pyrazoyl | 197–200 |
| 82 | A1-1 | 1-ethyl-5-methyl-3-pyrazolyl | 35–37 |
| 83 | A1-11 | 1-ethyl-5-methyl-3-pyrazolyl | 62–63 |
| 84 | A1-27 | 1-ethyl-5-methyl-3-pyrazolyl | |
| 85 | A1-43 | 1-ethyl-5-methyl-3-pyrazolyl | |
| 86 | A1-29 | 1-ethyl-5-methyl-3-pyrazolyl | 171–173 |
| 87 | A1-1 | 1-isopropyl-5-methyl-3-pyrazolyl | 156–158 |
| 88 | A1-29 | 1-isopropyl-5-methyl-3-pyrazolyl | 206–208 |
| 89 | A1-40 | 1-isopropyl-5-methyl-3-pyrazolyl | |
| 90 | A1-1 | 1-methyl-1,4,5,6-tetrahydrocyclopentapyrazol-3-yl | 187–188 |
| 91 | A1-28 | 1-methyl-1,4,5,6-tetrahydrocyclopentapyrazol-3-yl | |
| 92 | A1-30 | 1-methyl-1,4,5,6-tetrahydrocyclopentapyrazol-3-yl | |
| 93 | A1-40 | 1-methyl-1,4,5,6-tetrahydrocyclopentapyrazol-3-yl | |
| 94 | A1-1 | 1-methyl-4,5,6,7-tetrahydrobenzopyrazol-3-yl | 157–158 |
| 95 | A1-26 | 1-methyl-4,5,6,7-tetrahydrobenzopyrazol-3-yl | 134–135 |
| 96 | A1-43 | 1-methyl-4,5,6,7-tetrahydrobenzopyrazol-3-yl | |
| 97 | A1-2 | 1-methyl-4,5,6,7-tetrahydrobenzopyrazol-3-yl | |
| 98 | A1-1 | 1,3-dimethyl-5-pyrazolyl | 158–162 |
| 99 | A1-30 | 1,3-dimethyl-5-pyrazolyl | 203 |
| 100 | A1-29 | 1,3-dimethyl-5-pyrazolyl | >230 |
| 101 | A1-1 | 1-methyl-4-pyrazolyl | 174–178 |
| 102 | A1-30 | 1-methyl-4-pyrazolyl | 208 |
| 103 | A6-1 | 1-methyl-4-pyrazolyl | 174–180 |
| 104 | A9-1 | 1-methyl-4-pyrazolyl | 220–227 |
| 105 | A1-1 | 5-cyclopropyl-1-methyl-3-pyrazolyl | 150–152 |
| 106 | A1-27 | 5-cyclopropyl-1-methyl-3-pyrazolyl | |
| 107 | A1-30 | 5-cyclopropyl-1-methyl-3-pyrazolyl | 148–150 |
| 108 | A1-40 | 5-cyclopropyl-1-methyl-3-pyrazolyl | |
| 109 | A1-1 | 5-ethyl-1-methyl-3-pyrazolyl | - |
| 110 | A1-15 | 5-ethyl-1-methyl-3-pyrazolyl | |
| 111 | A1-30 | 5-ethyl-1-methyl-3-pyrazolyl | |
| 112 | A1-43 | 5-ethyl-1-methyl-3-pyrazolyl | |
| 113 | A1-28 | 1,4-dimethyl-2-imidazolyl | 230–231 |
| 114 | A1-1 | 1,4-dimethyl-2-imidazolyl | |
| 115 | A1-28 | 1-methyl-2-imidazolyl | 162–165 |
| 116 | A1-1 | 1-methyl-2-imidazolyl | |
| 117 | A1-29 | 1-methyl-2-imidazolyl | |
| 118 | A1-1 | 1-methyl-5-imidazolyl | 220 |
| 119 | A1-26 | 1-methyl-5-imidazolyl, Na salt | >300 |
| 120 | A1-30 | 1-methyl-5-imidazolyl | 255 |
| 121 | A1-30 | 1-methyl-5-imidazolyl Na salt | >300 |
| 122 | A1-40 | 1-methyl-5-imidazolyl | 260–265 |
| 123 | A1-29 | 1-methyl-5-imidazolyl | 295–300 |
| 124 | A1-1 | 2-methyl-4-oxazolyl | |
| 125 | A1-26 | 2-methyl-4-oxazolyl | |
| 126 | A1-30 | 2-methyl-4-oxazolyl | |
| 127 | A1-44 | 2-methyl-4-oxazolyl | |
| 128 | A1-1 | 2-cyclopropyl-4-oxazolyl | 110–112 |
| 129 | A1-2 | 2-cyclopropyl-4-oxazolyl | |
| 130 | A1-27 | 2-cyclopropyl-4-oxazolyl | 164–166 |
| 131 | A9-1 | 2-cyclopropyl-4-oxazolyl | |
| 132 | A1-1 | 1,2,3-thiadiazolyl-4-yl | 110 |
| 133 | A1-28 | 1,2,3-thiadiazolyl-4-yl | 173–176 |
| 134 | A1-29 | 1,2,3-thiadiazolyl-4-yl | >230 |
| 135 | A1-33 | 1,2,3-thiadiazolyl-4-yl | 139 |
| 136 | A1-1 | 4-methyl-1,2,3-thiadiazolyl-5-yl | |
| 137 | A1-28 | 4-methyl-1,2,3-thiadiazol-5-yl | |
| 138 | A1-27 | 4-chloro-1,5-dimethyl-3-pyrazolyl | 198–200 |
| 139 | A1-1 | 5-phenyl-3-isoxazolyl | 205–206 |
| 140 | A1-11 | 4-bromo-1,5-dimethyl-3-pyrazolyl | >210 |
| 141 | A1-26 | 1,5-dimethyl-3-pyrazolyl | 146–147 |
| 142 | A1-22 | 1,5-dimethyl-3-pyrazolyl | 152–153 |
| 143 | A1-28 | 5-methyl-3-isoxazolyl | 190–191 |
| 144 | A2-4 | 1,5-dimethyl-3-pyrazolyl | 191–192 |
| 145 | A1-49 | 1,5-dimethyl-3-pyrazolyl | 153–155 |
| 146 | A1-1 | 1,5-dimethyl-3-pyrazolyl, Na salt | >220 |
| 147 | A1-1 | 1,5-dimethyl-3-pyrazolyl, Ca salt | >220 |
| 148 | A1-11 | 1-methyl-1,4,5,6-tetrahydrocyclopentapyrazol-3-yl | 184–187 |
| 149 | A1-27 | 5-methyl-3-isoxazolyl | 160–161 |
| 150 | A1-22 | 5-methyl-3-isoxazolyl | 160–162 |
| 151 | A1-10 | 2-cyclopropyl-4-oxazolyl | 150–152 |
| 152 | A1-30 | 2-cyclopropyl-4-oxazolyl | 131–132 |
| 153 | A1-22 | 2-cyclopropyl-4-oxazolyl | 129–131 |
| 154 | A1-44 | 1,5-dimethyl-3-pyrazolyl | 83–85 |
| 155 | A6-1 | 1,5-dimethyl-3-pyrazolyl | 130–132 |
| 156 | A1-9 | 5-cyclopropyl-1-methyl-3-pyrazolyl | 100–101 |
| 157 | A1-9 | 4-chloro-1,5-dimethyl-3-pyrazolyl | 210–212 |
| 158 | A1-9 | 4-chloro-1,5-dimethyl-3-pyrazolyl | 194–195 |
| 159 | A2-4 | 4-bromo-1,5-dimethyl-3-pyrazolyl | 199 |
| 160 | A1-22 | 4-bromo-1,5-dimethyl-3-pyrazolyl | 175–177 |
| 161 | A1-18 | 4-bromo-1,5-dimethyl-3-pyrazolyl | 155–157 |
| 162 | A1-1 | 1,4,5-trimethyl-3-pyrazolyl, Na salt | >220 |
| 163 | A1-30 | 1,4,5-trimethyl-3-pyrazolyl | 148–150 |
| 164 | A1-1 | 4,5-diethyl-1-methyl-3-pyrazolyl | 154–156 |
| 165 | A1-1 | 4,5-diethyl-1-methyl-3-pyrazolyl, Na salt | 90–92 |
| 166 | A1-2 | 4,5-diethyl-1-methyl-3-pyrazolyl | 137–139 |
| 167 | A1-2 | 4,5-diethyl-1-methyl-3-pyrazolyl, Na salt | 157–159 |
| 168 | A1-9 | 4,5-diethyl-1-methyl-3-pyrazolyl | 167–169 |
| 169 | A1-9 | 4,5-diethyl-1-methyl-3-pyrazolyl, Na salt | 130–132 |
| 170 | A1-10 | 4,5-diethyl-1-methyl-3-pyrazolyl | 116–118 |
| 171 | A2-4 | 4,5-diethyl-1-methyl-3-pyrazolyl | 121–123 |
| 172 | A1-29 | 4,5-diethyl-1-methyl-3-pyrazolyl | 128–130 |
| 173 | A1-29 | 4,5-diethyl-1-methyl-3-pyrazolyl, Na salt | 141–143 |
| 174 | A1-27 | 4,5-diethyl-1-methyl-3-pyrazolyl, Na salt | >220 |
| 175 | A1-30 | 4,5-diethyl-1-methyl-3-pyrazolyl | 96–98 |
| 176 | A1-30 | 4,5-diethyl-1-methyl-3-pyrazolyl, Na salt | >220 |
| 177 | A1-22 | 4,5-diethyl-1-methyl-3-pyrazolyl | 93–95 |
| 178 | A1-22 | 4,5-diethyl-1-methyl-3-pyrazolyl, Na salt | 82–84 |
| 179 | A1-28 | 4,5-diethyl-1-methyl-3-pyrazolyl | 150–152 |
| 180 | A1-28 | 4,5-diethyl-1-methyl-3-pyrazolyl, Na salt | 120–122 |
| 181 | A1-9 | 1-methyl-4,5,6,7-tetrahydrobenzopyrazol-3-yl | 177–178 |
| 182 | A1-10 | 1-methyl-4,5,6,7-tetrahydrobenzopyrazol-3-yl | 180–181 |
| 183 | A1-29 | 1-methyl-4,5,6,7-tetrahydrobenzopyrazol-3-yl | 210 |

TABLE 1-continued

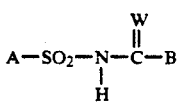

| No. | A | B | M.p. (°C.) |
|---|---|---|---|
| 184 | A1-30 | 1-methyl-4,5,6,7-tetrahydro-benzopyrazol-3-yl | 167–168 |
| 185 | A1-27 | 1-methyl-4,5,6,7-tetrahydro-benzopyrazol-3-yl | 161–162 |
| 186 | A1-28 | 1-methyl-4,5,6,7-tetrahydro-benzopyrazol-3-yl | 125–126 |
| 187 | A1-1 | 1-ethyl-5-methyl-3-pyrazolyl, Na salt | 168–170 |
| 188 | A1-2 | 1-ethyl-5-methyl-3-pyrazolyl | 90–92 |
| 189 | A1-30 | 1-ethyl-5-methyl-3-pyrazolyl | 120–121 |
| 190 | A1-28 | 1-ethyl-5-methyl-3-pyrazolyl | 133–135 |
| 191 | A1-1 | 1-methyl-3-phenyl-4-pyrazolyl | 32–34 |
| 192 | A1-30 | 1-methyl-5-phenyl-4-pyrazolyl | 199–201 |

It is also possible in a similar way to prepare further compounds of the structure $$A-SO_2-N(H)-\overset{W}{\overset{\|}{C}}-B$$

where
A can be a radical from the group E1 to E97
B can be a radical from the group G1 to G12
X can be O, S or $NR^9$
W can be O or S
$R^8$ can be a radical from the group L1 to L140
$R^9$ can be a radical from the group V1 to V35 for example, and any combination of E, G, L, V, W and X is possible,
or where
A can be a radical from the group E1 to E97
B can be a radical from the group G13 to G14
X can be O or S
W can be O or S
$R^8$ can be a radical from the group L1 to L140 for example, and any combination of E, G, L, W and X is possible,
or where
A can be a radical from the group E1 to E97
B can be the radical G15
X can be N
W can be O or S
$R^{10}$ can be a radical from the group Y1 to Y16
$R^{11}$ can be a radical from the group Z1 to Z13 for example, and any combination of E, G, W, Y and Z is possible Examples of possible meanings of A, B, $R^8$, $R^9$, $R^{10}$ and $R^{11}$ are the following:

| Comp. No. | A |
|---|---|
| E1 | $2\text{-}CO_2CH_3\text{---}C_6H_4$ |
| E2 | $2\text{-}CO_2CH_2CH_3\text{---}C_6H_4$ |
| E3 | $2\text{-}CO_2CH(CH_3)_2\text{---}C_6H_4$ |
| E4 | $2\text{-}CO_2CH_3\text{-}6\text{-}Cl\text{---}C_6H_3$ |
| E5 | $2\text{-}CO_2CH_3\text{-}6\text{-}OCH_3\text{---}C_6H_3$ |
| E6 | $2\text{-}CO_2CH_3\text{-}6\text{-}CH_3\text{---}C_6H_3$ |
| E7 | $2\text{-}CO_2CH_3\text{-}3\text{-}Cl\text{---}C_6H_3$ |
| E8 | $2\text{-}CO_2CH_3\text{-}3\text{-}F\text{---}C_6H_3$ |
| E9 | $2\text{-}CO_2CH_3\text{-}6\text{-}F\text{---}C_6H_3$ |
| E10 | $2\text{-}CO_2CH_3\text{-}4\text{-}Cl\text{---}C_6H_3$ |
| E11 | $2\text{-}CO_2CH_3\text{-}5\text{-}Cl\text{---}C_6H_3$ |
| E12 | $2\text{-}CO_2CH_3\text{-}5\text{-}F\text{---}C_6H_3$ |
| E13 | $2\text{-}CO_2CH_3\text{-}5\text{-}OCH_3\text{---}C_6H_3$ |
| E14 | $2\text{-}CO_2CH_3\text{-}5\text{-}OCHF_2\text{---}C_6H_3$ |
| E15 | $2\text{-}CON(CH_3)_2\text{---}C_6H_4$ |
| E16 | $2\text{-}CON(CH_3)_2\text{-}3\text{-}Cl\text{---}C_6H_3$ |
| E17 | $2\text{-}CON(CH_3)_2\text{-}3\text{-}F\text{---}C_6H_3$ |
| E18 | $2\text{-}CH_3\text{---}C_6H_4$ |
| E19 | $2\text{-}CH_2Cl\text{---}C_6H_4$ |
| E20 | $2\text{-}CH_2OCH_3\text{---}C_6H_4$ |
| E21 | $2\text{-}CH_2SCH_3\text{---}C_6H_4$ |
| E22 | $2\text{-}CF_3\text{---}C_6H_4$ |
| E23 | $2\text{-}CH_3\text{-}5\text{-}Cl\text{---}C_6H_3$ |
| E24 | $2,5\text{-}(CH_3)_2\text{---}C_6H_3$ |
| E25 | $2\text{-}CH_3\text{-}5\text{-}OCH_3\text{---}C_6H_3$ |
| E26 | $2\text{-}F\text{---}C_6H_4$ |
| E27 | $2,6\text{-}F_2\text{---}C_6H_3$ |
| E28 | $2\text{-}Cl\text{---}C_6H_4$ |
| E29 | $2,6\text{-}Cl_2\text{---}C_6H_3$ |
| E30 | $2\text{-}Cl\text{-}6\text{-}CH_3\text{---}C_6H_3$ |
| E31 | $2\text{-}Cl\text{-}6\text{-}OCH_3\text{---}C_6H_3$ |
| E32 | $2\text{-}Cl\text{-}5\text{-}CO_2CH_3\text{---}C_6H_3$ |
| E33 | $2,5\text{-}Cl_2\text{---}C_6H_3$ |
| E34 | $2,3\text{-}Cl_2\text{---}C_6H_3$ |
| E35 | $2,5,6\text{-}Cl_3\text{---}C_6H_2$ |
| E36 | $2,4,6\text{-}Cl_3\text{---}C_6H_2$ |
| E37 | $2\text{-}Br\text{---}C_6H_4$ |
| E38 | $2,6\text{-}Br_2\text{---}C_6H_3$ |
| E39 | $2\text{-}CN\text{---}C_6H_4$ |
| E40 | $2\text{-}OCH_3\text{---}C_6H_4$ |
| E41 | $2\text{-}OCH_2CH_3\text{---}C_6H_4$ |
| E42 | $2\text{-}OCH(CH_3)_2\text{---}C_6H_4$ |
| E43 | $2\text{-}OCH_2CH_2Cl\text{---}C_6H_4$ |
| E44 | $2\text{-}OCH_2CH_2OCH_3\text{---}C_6H_4$ |
| E45 | $2\text{-}OCH_2CF_3$ |
| E46 | $2\text{-}OCF_3$ |
| E47 | $2\text{-}OCF_2H\text{---}C_6H_4$ |
| E48 | $2\text{-}OCH_3\text{-}5\text{-}Br\text{---}C_6H_3$ |
| E49 | $2,5\text{-}(OCH_3)_2\text{---}C_6H_3$ |
| E50 | $2,5\text{-}(OCH_2CF_3)_2\text{---}C_6H_3$ |
| E51 | $2\text{-}SCH_3\text{---}C_6H_4$ |
| E52 | $2\text{-}SCH_2CH_3\text{---}C_6H_4$ |
| E53 | $2\text{-}SO_2CH_3\text{---}C_6H_4$ |
| E54 | $2\text{-}SO_2CH_2CH_3\text{---}C_6H_4$ |
| E55 | $2\text{-}SO_2CH_2CH_2CH_3\text{---}C_6H_4$ |
| E56 | $2\text{-}SO_2CH(CH_3)_2\text{---}C_6H_4$ |
| E57 | $2\text{-}SO_2N(CH_3)_2\text{---}C_6H_4$ |
| E58 | $2\text{-}OSO_2CH_3\text{---}C_6H_4$ |
| E59 | $2\text{-}OSO_2CH_2CH_3\text{---}C_6H_4$ |
| E60 | $2\text{-}COCH_3\text{---}C_6H_4$ |
| E61 | $2\text{-}C_6H_5\text{---}C_6H_4$ |
| E62 | Pyrid-2-yl |
| E63 | $3\text{-}CO_2CH_3\text{-}pyrid\text{-}2\text{-}yl$ |
| E64 | $3\text{-}CO_2CH_2CH_3\text{-}pyrid\text{-}2\text{-}yl$ |
| E65 | $3\text{-}CON(CH_3)_2\text{-}pyrid\text{-}2\text{-}yl$ |
| E66 | 3-Cl-pyrid-2-yl |
| E67 | $3\text{-}CF_3\text{-}pyrid\text{-}2\text{-}yl$ |
| E68 | $3\text{-}OCH_2CH_3\text{-}pyrid\text{-}2\text{-}yl$ |
| E69 | $3\text{-}SO_2CH_3\text{-}pyrid\text{-}2\text{-}yl$ |
| E70 | $3\text{-}SO_2CH_2CH_3\text{-}pyrid\text{-}2\text{-}yl$ |
| E71 | $3\text{-}SOCH_3\text{-}pyrid\text{-}2\text{-}yl$ |
| E72 | $3\text{-}SOC_2H_5\text{-}pyrid\text{-}2\text{-}yl$ |
| E73 | $3\text{-}SO_2N(CH_3)_2\text{-}pyrid\text{-}2\text{-}yl$ |
| E74 | $3\text{-}SO_2NHCH(CH_3)_2\text{-}pyrid\text{-}2\text{-}yl$ |
| E75 | Pyrid-3-yl |
| E76 | $2\text{-}CON(CH_3)_2\text{-}pyrid\text{-}3\text{-}yl$ |
| E77 | Thien-2-yl |
| E78 | 3-Cl-thien-2-yl |
| E79 | 4-Cl-thien-2-yl |
| E80 | 5-Cl-thien-2-yl |
| E81 | $3\text{-}CO_2CH_3\text{-}thien\text{-}2\text{-}yl$ |
| E82 | $2\text{-}CO_2CH_3\text{-}thien\text{-}3\text{-}yl$ |
| E83 | $2\text{-}CON(CH_3)_2\text{-}thien\text{-}3\text{-}yl$ |
| E84 | $4\text{-}CO_2CH_3\text{-}thien\text{-}3\text{-}yl$ |
| E85 | Naphth-1-yl |
| E86 | $2\text{-}CO_2CH_3\text{-}naphth\text{-}1\text{-}yl$ |
| E87 | 2-Cl-naphth-1-yl |
| E88 | $8\text{-}CO_2CH_3\text{-}naphth\text{-}1\text{-}yl$ |
| E89 | 8-Cl-naphth-1-yl |
| E90 | $8\text{-}OCH_3\text{-}naphth\text{-}1\text{-}yl$ |
| E91 | $8\text{-}OCH_2CH_2OCH_3\text{-}naphth\text{-}1\text{-}yl$ |
| E92 | $8\text{-}OCH_2CH_2Cl\text{-}naphth\text{-}1\text{-}yl$ |
| E93 | Naphth-2-yl |

-continued

| Comp. No. | |
|---|---|
| E94 | 1-CO$_2$CH$_3$-naphth-2-yl |
| E95 | 1-Cl-naphth-2-yl |
| E96 | 1-OCH$_2$CH$_2$OCH$_3$-naphth-2-yl |
| E97 | 1-OCH$_2$CH$_2$Cl-naphth-2-yl |

B

G1 — R$^8$, R$^8$, R$^8$, X ring (with implicit methyl)

G2 — variant ring with R$^8$ substituents

G3 — N-containing 5-ring with R$^8$ substituents

G4 — N-containing ring variant

G5 — N-containing ring variant

G6 — R$^8$, N, X ring

G7 — R$^8$, N, X ring variant

G8 — R$^8$, N, X ring variant

G9 — R$^8$, N=N, X ring

G10 — R$^8$, N, N, X ring

G11 — N—N, R$^8$, X ring

G12 — N, R$^8$, X, N ring

G13 — N, R$^8$, X, N ring variant

G14 — R$^8$, N, X, N ring

G15 — N, R$^{10}$, X, N, R$^{11}$ ring

| | R$^8$ |
|---|---|
| L1 | H |
| L2 | F |
| L3 | Cl |
| L4 | Br |
| L5 | J |
| L6 | CN |
| L7 | NO$_2$ |
| L8 | CH$_3$ |
| L9 | C$_2$H$_5$ |
| L10 | n-C$_3$H$_7$ |
| L11 | i-C$_3$H$_7$ |
| L12 | n-C$_4$H$_9$ |
| L13 | i-C$_4$H$_9$ |
| L14 | s-C$_4$H$_9$ |
| L15 | tert.-C$_4$H$_9$ |
| L16 | CH$_2$F |
| L17 | CH$_2$Cl |
| L18 | CH$_2$Br |
| L19 | CHF$_2$ |
| L20 | CF$_3$ |
| L21 | CCl$_3$ |
| L22 | CH$_2$—CH$_2$F |
| L23 | CH$_2$—CH$_2$Cl |
| L24 | CH$_2$—CHF$_2$ |
| L25 | CH$_2$—CF$_3$ |
| L26 | CH$_2$—CCl$_3$ |
| L27 | CF$_2$—CF$_3$ |
| L28 | CH$_2$—O—CH$_3$ |
| L29 | CH$_2$—CH$_2$—OCH$_3$ |
| L30 | CH(CH$_3$)OCH$_3$ |
| L31 | CH(CH$_3$)CH$_2$OCH$_3$ |
| L32 | CH$_2$OC$_2$H$_5$ |
| L33 | CH$_2$C$_6$H$_5$ |
| L34 | cyclo-C$_3$H$_5$ |
| L35 | cyclo-C$_4$H$_7$ |
| L36 | cyclo-C$_5$H$_9$ |
| L37 | cyclo-C$_6$H$_{11}$ |
| L38 | Tetrahydropyran-2-yl |
| L39 | Tetrahydropyran-3-yl |
| L40 | Tetrahydrofuran-2-yl |
| L41 | Tetrahydrofuran-3-yl |
| L42 | Thien-2-yl |
| L43 | Thien-3-yl |
| L44 | Furan-2-yl |
| L45 | Furan-3-yl |
| L46 | 1-Methylpyrazol-3-yl |
| L47 | 1-Methylpyrazol-4-yl |
| L48 | 1-Methylpyrazol-5-yl |
| L49 | 1-Ethylpyrazol-3-yl |
| L50 | 1-Ethylpyrazol-4-yl |
| L51 | 1-Ethylpyrazol-5-yl |
| L52 | OCH$_3$ |
| L53 | OC$_2$H$_5$ |
| L54 | OCH(CH$_3$)$_2$ |
| L55 | OCH$_2$CH$_2$Cl |
| L56 | OCH$_2$CH$_2$OCH$_3$ |
| L57 | OCF$_3$ |
| L58 | OCHF$_2$ |
| L59 | OCH$_2$CF$_3$ |
| L60 | OC$_6$H$_5$ |

-continued

| Comp. No. | |
|---|---|
| L61 | OCH$_2$C$_6$H$_5$ |
| L62 | SCH$_3$ |
| L63 | SCH$_2$CH$_3$ |
| L64 | SC$_6$H$_5$ |
| L65 | SCH$_2$C$_6$H$_5$ |
| L66 | CH$_2$—CH=CH$_2$ |
| L67 | CH(CH$_3$)—CH=CH$_2$ |
| L68 | CH$_2$—C(CH$_3$)=CH$_2$ |
| L69 | CH$_2$—CH=CH—CH$_3$ |
| L70 | CH$_2$—C≡CH |
| L71 | CH(CH$_3$)—C≡CH |
| L72 | CH$_2$—C≡C—CH$_3$ |
| L73 | C$_6$H$_5$ |
| L74 | 2-CH$_3$—C$_6$H$_4$ |
| L75 | 3-CH$_3$—C$_6$H$_4$ |
| L76 | 4-CH$_3$—C$_6$H$_4$ |
| L77 | 2-CF$_3$—C$_6$H$_4$ |
| L78 | 3-CF$_3$—C$_6$H$_4$ |
| L79 | 4-CF$_3$—C$_6$H$_4$ |
| L80 | 2-F—C$_6$H$_4$ |
| L81 | 3-F—C$_6$H$_4$ |
| L82 | 4-F—C$_6$H$_4$ |
| L83 | 2-Cl—C$_6$H$_4$ |
| L84 | 3-Cl—C$_6$H$_4$ |
| L85 | 4-Cl—C$_6$H$_4$ |
| L86 | 2-NO$_2$—C$_6$H$_4$ |
| L87 | 3-NO$_2$—C$_6$H$_4$ |
| L88 | 4-NO$_2$—C$_6$H$_4$ |
| L89 | 2-CH$_3$—C$_6$H$_4$ |
| L90 | 3-CH$_3$O—C$_6$H$_4$ |
| L91 | 4-CH$_3$O—C$_6$H$_4$ |
| L92 | COCH$_3$ |
| L93 | COCH$_2$CH$_3$ |
| L94 | CO(cycloC$_3$H$_5$) |
| L95 | COCH$_2$Cl |
| L96 | COCH$_2$Br |
| L97 | COCH$_2$F |
| L98 | COCF$_3$ |
| L99 | COCH$_2$OCH$_3$ |
| L100 | CO$_2$H |
| L101 | CO$_2$CH$_3$ |
| L102 | CO$_2$CH$_2$CH$_3$ |
| L103 | CO$_2$CH(CH$_3$)$_2$ |
| L104 | CO$_2$CH$_2$CF$_3$ |
| L105 | CO$_2$CH$_2$CH$_2$OCH$_3$ |
| L106 | CO$_2$CH$_2$C$_6$H$_5$ |
| L107 | CONH$_2$ |
| L108 | CONHCH$_3$ |
| L109 | CON(CH$_3$)$_2$ |
| L110 | CONHC$_2$H$_5$ |
| L111 | CON(C$_2$H$_5$)$_2$ |
| L112 | CONHCH(CH$_3$)$_2$ |
| L113 | CONHCH$_2$C$_6$H$_5$ |
| L114 | CONHC$_6$H$_5$ |
| L115 | CONHOCH$_3$ |
| L116 | CONHOC$_2$H$_5$ |
| L117 | SO$_2$N(CH$_3$)$_2$ |
| L118 | SO$_2$NCH$_3$(C$_2$H$_5$) |
| L119 | SO$_2$N(C$_2$H$_5$)$_2$ |
| L120 | SO$_2$NHCH$_3$ |
| L121 | SO$_2$NHC$_2$H$_5$ |
| L122 | SO$_2$OCH$_3$ |
| L123 | SO$_2$OC$_2$H$_5$ |
| L124 | SO$_2$OCH(CH$_3$)$_2$ |
| L125 | SO$_2$OCH$_2$CH$_2$Cl |
| L126 | SO$_2$OCH$_2$CF$_3$ |
| L127 | OSO$_2$CH$_3$ |
| L128 | OSO$_2$C$_2$H$_5$ |
| L129 | OSO$_2$CH(CH$_3$)$_2$ |
| L130 | OSO$_2$N(CH$_3$)$_2$ |
| L131 | SOCH$_3$ |
| L132 | SOC$_2$H$_5$ |
| L133 | SOCH(CH$_3$)$_2$ |
| L134 | SOC$_6$H$_5$ |
| L135 | SO$_2$CH$_3$ |
| L136 | SO$_2$CH$_2$CH$_3$ |
| L137 | SO$_2$CH(CH$_3$)$_2$ |
| L138 | SO$_2$CH$_2$CH$_2$CH$_3$ |
| L139 | two vicinal R$^8$ radicals together form a trimethylene chain |
| L140 | two vicinal R$^8$ radicals together form a tetramethylene chain |

| Comp. No. | |
|---|---|
| | R$^9$ |
| V1 | H |
| V2 | CH$_3$ |
| V3 | CH$_2$CH$_3$ |
| V4 | CH$_2$CH$_2$F |
| V5 | CH$_2$CF$_3$ |
| V6 | CH$_2$CH$_2$Cl |
| V7 | CH$_2$CH$_2$OCH$_3$ |
| V8 | CH$_2$C$_6$H$_5$ |
| V9 | CH(CH$_3$)$_2$ |
| V10 | cyclo-C$_3$H$_5$ |
| V11 | cyclo-C$_4$H$_7$ |
| V12 | cyclo-C$_5$H$_9$ |
| V13 | C$_6$H$_5$ |
| V14 | 2-CH$_3$—C$_6$H$_4$ |
| V15 | 2-C$_2$H$_5$—C$_6$H$_4$ |
| V16 | 2,6-(CH$_3$)$_2$—C$_6$H$_3$ |
| V17 | 2,6-(C$_2$H$_5$)$_2$—C$_6$H$_3$ |
| V18 | 2-CH$_3$-6-C$_2$H$_5$—C$_6$H$_3$ |
| V19 | 2-Cl—C$_6$H$_4$ |
| V20 | 2,4-Cl$_2$—C$_6$H$_3$ |
| V21 | 2,6-Cl$_2$—C$_6$H$_3$ |
| V22 | 2,4,6-Cl$_3$—C$_6$H$_2$ |
| V23 | 2,6-Cl$_2$-4-CF$_3$—C$_6$H$_2$ |
| V24 | 2-Cl-4-CF$_3$—C$_6$H$_3$ |
| V25 | CH$_2$—CH=CH$_2$ |
| V26 | CH=CH$_2$ |
| V27 | CH$_2$—C≡CH |
| V28 | CH$_2$C$_6$H$_5$ |
| V29 | COCH$_3$ |
| V30 | COC$_2$H$_5$ |
| V31 | COC$_6$H$_5$ |
| V32 | CH$_2$F |
| V33 | CHF$_2$ |
| V34 | CF$_3$ |
| V35 | CF$_2$Cl |
| | R$^{10}$ |
| Y1 | C$_6$H$_5$ |
| Y2 | 2-Cl—C$_6$H$_4$ |
| Y3 | 2-F—C$_6$H$_4$ |
| Y4 | 2-CH$_3$—C$_6$H$_3$ |
| Y5 | 2-CF$_3$—C$_6$H$_3$ |
| Y6 | 2-OCH$_3$—C$_6$H$_3$ |
| Y7 | 2,3-Cl$_2$—C$_6$H$_3$ |
| Y8 | 2,4-Cl$_2$—C$_6$H$_3$ |
| Y9 | 2,5-Cl$_2$—C$_6$H$_3$ |
| Y10 | 2,6-Cl$_2$—C$_6$H$_3$ |
| Y11 | 2,4,6-Cl$_3$—C$_6$H$_2$ |
| Y12 | CH$_2$C$_6$H$_5$ |
| Y13 | OC$_6$H$_5$ |
| Y14 | OCH$_2$C$_6$H$_5$ |
| Y15 | SC$_6$H$_5$ |
| Y16 | SCH$_2$C$_6$H$_5$ |
| | R$^{11}$ |
| Z1 | H |
| Z2 | C$_6$H$_5$ |
| Z3 | 2-Cl—C$_6$H$_4$ |
| Z4 | 2-F—C$_6$H$_4$ |
| Z5 | 2-CH$_3$—C$_6$H$_4$ |
| Z6 | 2-CF$_3$—C$_6$H$_4$ |
| Z7 | 2-OCH$_3$—C$_6$H$_4$ |
| Z8 | 2,4-Cl$_2$—C$_6$H$_3$ |
| Z9 | 2,6-Cl$_2$—C$_6$H$_3$ |
| Z10 | 2,6-F$_2$—C$_6$H$_3$ |
| Z11 | 2,6-(CH$_3$)$_2$—C$_6$H$_3$ |
| Z12 | 2-Cl-4-CF$_3$—C$_6$H$_3$ |
| Z13 | 2,6-Cl$_2$-4-CF$_3$—C$_6$H$_2$ |

EXAMPLES OF USE

A Herbicidal action

The herbicidal action of the sulfonamides of the formula I was demonstrated in glasshouse tests:

The plants were grown in plastic flower pots containing loamy sand with about 3% humus as substrate. The seeds of the test plants were sown separately for each species.

In the case of pre-emergence treatment, the active ingredients suspended or emulsified in water were applied directly after sowing using finely dispersing nozzles. The pots were lightly watered in order to promote germination and growth and were then covered with transparent plastic covers until the plants had started to grow. This covering results in uniform germination of the test plants unless this has been impaired by the active ingredients. The application rates were 0.125 kg/ha active substance.

For post-emergence treatment, the test plants were treated with the active ingredients suspended or emulsified in water after they had grown to a height of from 3 to 15 cm depending on species. The application rate for the post-emergence treatment was 0.25 kg/ha active substance.

The plants were kept at 10°–25° C. or 20°–35° C. depending on the species. The test period lasted 2 to 4 weeks during which time the plants were tended and their reaction to the individual treatments was evaluated.

A scale from 0 to 100 was used for evaluation. 100 means no emergence of the parts or complete destruction of, at least, the above-ground parts and zero means no damage or normal growth.

The plants used in the glasshouse tests comprised the following species:

| Latin name | English Name |
| --- | --- |
| Abutilon theophr. | Chinese hemp |
| Chenopodium album | white goosefoot |
| Triticum aestivum | summer wheat |

When 0.25 kg/ha active substance was employed in the post-emergence procedure there is very good control with Example 40 of broad-leaved weeds while the exemplary crop wheat tolerates the treatment.

B Growth-regulating action

The growth-regulating properties of the test substances were determined by growing test plants on substrate with an adequate nutrient supply in plastic containers of diameter about 12.5 cm.

The test substances in aqueous formulations were sprayed in the post-emergence method onto the plants. The growth-regulating action was established from the measured height of growth at the end of the test. The measurements were related to the height of growth of untreated plants. 2-Chloroethyltrimethylammonium chloride was used as comparative substance A.

The reduction in longitudinal growth was accompanied by a simultaneous increase in leaf color intensity. The increased chlorophyll content suggests that the photosynthesis rate, and thus the yield, is increased.

The individual data are to be found in Tables B-1 and B-2 below.

TABLE B-1

| Summer wheat "Ralle"; post-emergence leaf treatment | | |
| --- | --- | --- |
| Chem. example No. | Concentration mg AS/container | Rel. growth height |
| Untreated | — | 100 |
| A | 1.5 | 82.2 |
|  | 1.5 | 73.1 |

TABLE B-2

| Summer barley "Aramir"; post-emergence leaf treatment | | |
| --- | --- | --- |
| Chem. example No. | Concentration mg AS/container | Rel. growth height |
| Untreated | — | 100 |
| A | 1.5 | 90.7 |
|  | 1.5 | 69.4 |

We claim:
1. A sulfonamide of the formula I

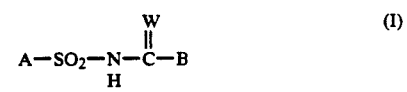

where
A is

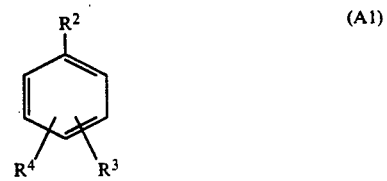

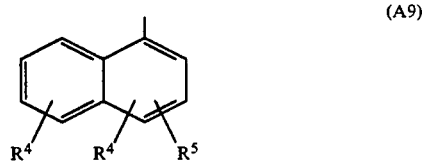

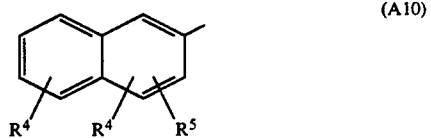

W is oxygen or sulfur;
B is 3-, 4- or 5-pyrazol disubstituted on carbon by $R^8$ and monosubstituted on nitrogen by $R^9$;
$R^2$ is halogen; cyano; thiocyano;
$C_1$–$C_6$-alkyl which is unsubstituted or substituted by at least one of the following: one to five halogens, or one of the following: $C_1$–$C_4$-alkoxy, $C_1$–$C_4$-haloalkoxy, $C_1$–$C_4$-alkylthio, $C_1$–$C_4$-haloalkylthio, phenyl, phenoxy or phenylthio, where each of the phenyls is unsubstituted or substituted by at least one of the following: one to five halogens, or one to three of the following: $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio or $C_1$–$C_4$-haloalkylthio; $C_3$–$C_6$-cycloalkyl, $C_3$–$C_8$-cycloalkoxy, $C_3$–$C_6$-cycloalkylthio, $C_5$–$C_6$-cycloalkenyl, $C_5$–$C_8$-cycloalkenyloxy or $C_5$–$C_8$-cycloalkenylthio, each of which is unsubstituted or substituted by at least one of the following: one to five halogens, or one to three of the following: $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio or $C_1$–$C_4$-haloalkylthio;
phenyl, phenoxy, benzyloxy or benzylthio, each of which is unsubstituted or substituted by at least one of the following: one to five halogens, or one to three of the following: cyano, nitro, $C_1$–$C_4$-alkyl, $C_1$-$C_4$-haloalkyl, $C_1$-$C_4$-alkoxy, haloalkoxy, $C_1$-$C_4$-alkylthio or $C_1$-$C_4$-haloalkylthio;

saturated, or unsaturated 5-7-membered heterocycle, said unsaturated 5-7 membered heterocycle having one or two double bonds, said saturated or unsaturated 5-7 membered heterocycle having one or two heteroatoms selected from nitrogen, oxygen and sulfur and which is unsubstituted or substituted by one or two of the following: halogen, cyano, nitro, $C_1$-$C_4$-alkyl, $C_1$-$C_4$-alkoxy, $C_1$-$C_4$-alkylthio, $C_1$-$C_4$-haloalkyl, $C_1$-$C_4$-haloalkoxy or $C_1$-$C_4$-haloalkylthio;

$C_1$-$C_4$-alkoxy or $C_1$-$C_4$-alkylthio, $C_2$-$C_6$-alkenyl or $C_2$-$C_6$-alkenyloxy or $C_2$-$C_6$-alkenylthio, $C_2$-$C_6$-alkynyl, $C_2$-$C_6$-alkynyloxy or $C_2$-$C_6$-alkynylthio, where the said alkoxy, alkylthio, alkenyl, alkynyl, alkenyloxy(thio) and alkynyloxy(thio) is unsubstituted or substituted by at least one of the following: one to five halogens, or one of the following: $C_1$-$C_4$-alkoxy, $C_1$-$C_4$-haloalkoxy, $C_1$-$C_4$-alkylthio, $C_1$-$C_4$-haloalkylthio; phenyl, phenoxy, phenylthio, benzyloxy or benzylthio; $COR^{12}$; $COQR^{13}$; $SO_2NR^{15}R^{16}$; $SO_2OR^{17}$; $OSO_2R^{18}$; $S(O)_nR^{19}$;

$R^3$ is $R^6$; $COQR^{13}$; $SO_2NR^{15}R^{16}$; $SO_2OR^{17}$; $OSO_2R^{18}$; $S(O)_nR^{19}$;

$R^4$ is hydrogen; halogen; cyano;

$C_1$-$C_4$-alkyl or $C_1$-$C_4$-alkyl substituted by one to five halogens; $C_1$-$C_4$-alkoxy; $C_1$-$C_4$-haloalkoxy; $C_1$-$C_4$-alkylthio; $C_1$-$C_4$-haloalkylthio;

$R^5$ is hydrogen; nitro or $R^2$;

$R^6$ is hydrogen; halogen; cyano;

$C_1$-$C_4$-alkyl, $C_1$-$C_4$-alkyl substituted by at least one of the following: one to five halogens, or one of the following:

$C_1$-$C_4$-alkoxy, $C_1$-$C_4$-haloalkoxy, $C_1$-$C_4$-alkylthio, $C_1$-$C_4$-haloalkylthio, OH, SH or cyano;

$C_1$-$C_4$-alkoxy, $C_1$-$C_4$-alkylthio, $C_1$-$C_4$-haloalkoxy or $C_1$-$C_4$-haloalkylthio, each of which is unsubstituted or substituted by the following: $C_1$-$C_4$-alkoxy, $C_1$-$C_4$-haloalkoxy, $C_1$-$C_4$-alkylthio or $C_1$-$C_4$-haloalkylthio;

$R^8$ is hydrogen; nitro; or $R^2$, or two vicinal $R^2$ together form a $C_3$ chain or a $C_4$-$C_6$ chain unsubstituted or in which one methylene is replaced by oxygen or $C_1$-$C_4$-alkylimino;

$R^9$ is $C_1$-$C_6$-alkyl which is unsubstituted or substituted by at least one of the following: one to five halogens, or one of the following: $C_1$-$C_4$-alkoxy; $C_1$-$C_4$-haloalkoxy; $C_1$-$C_4$-alkylthio;

$C_1$-$C_4$-haloalkylthio, phenyl, phenoxy or phenylthio, wherein cyclic groups are unsubstituted or substituted by at least one of the following: one to five halogens, or one to three of the following: cyano, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio or $C_1$-$C_4$-haloalkylthio;

$C_3$-$C_6$-cycloalkyl or $C_5$-$C_6$-cycloalkenyl, each of which is unsubstituted or substituted by at least one of the following: one to five halogens, or one to three of the following: $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio, or $C_1$-$C_4$-haloalkylthio;

phenyl which is unsubstituted or substituted by at least one of the following: one to five halogens, or one to three of the following: cyano, nitro, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio or $C_1$-$C_4$-haloalkylthio;

$C_2$-$C_6$-alkenyl or $C_2$-$C_6$-alkynyl, each of which is unsubstituted or substituted by at least one of the following: one to five halogens, or one of the following: $C_1$-$C_4$-alkoxy, $C_1$-$C_4$-haloalkoxy, $C_1$-$C_4$-alkylthio or $C_1$-$C_4$-haloalkylthio, phenyl, phenoxy, phenylthio, benzyloxy or benzylthio;

$COR^{21}$;

$R^{10}$ is phenyl, benzyl, phenoxy, benzyloxy, phenylthio or benzylthio, each of which is unsubstituted or substituted by at least one of the following: one to five halogens, or one to three of the following: cyano, nitro, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio or $C_1$-$C_4$-haloalkylthio;

$R^{11}$ is hydrogen; phenyl or benzyl, each of which is unsubstituted or substituted by at least one of the following: one to five halogens, or one to three of the following:

cyano, nitro, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio or $C_1$-$C_4$-haloalkylthio;

$R^{12}$ is $C_1$-$C_4$-alkyl which is unsubstituted or substituted by halogen or methoxy; $C_3$-$C_5$-cycloalkyl which is unsubstituted or substituted by chlorine or fluorine; $C_3$-$C_4$-alkenyl;

Q is oxygen or $NR^{14}$;

$R^{13}$ is hydrogen;

$C_1$-$C_6$-alkyl, $C_1$-$C_6$-alkyl substituted by one to three of the following: halogen, $C_1$-$C_4$-alkoxy, $C_1$-$C_4$-alkylthio, $C_1$-$C_4$-haloalkoxy, $C_1$-$C_4$-alkoxy-$C_1$-$C_2$-alkoxy, $C_3$-$C_6$-cycloalkyl, or phenyl;

$C_3$-$C_6$-cycloalkyl, which is substituted one to three times by $C_1$-$C_4$-alkyl; $C_3$-$C_6$-alkenyl; $C_3$-$C_6$-alkynyl;

phenyl, phenyl substituted by at least one of the following:

one to five halogens, or one to three of the following: cyano, nitro, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio or $C_1$-$C_4$-haloalkylthio;

$R^{14}$ is $OR^{20}$; $R^{13}$ or forms together with another $R^{13}$ a $C_4$-$C_6$-alkylene chain or a $C_4$-$C_6$-alkylene chain in which one methylene is replaced by oxygen or $C_1$-$C_4$-alkylimino;

$R^{15}$ is $C_1$-$C_4$-alkyl; $C_3$-$C_4$-alkenyl; $C_3$-$C_4$-alkynyl; cyclopropylmethyl; $C_3$-$C_4$-cycloalkyl;

$R^{16}$ is hydrogen; $C_1$-$C_4$-alkyl; $C_3$-$C_4$-alkenyl; or forms together with $R^{15}$ a $C_4$-$C_6$-alkylene chain in which one methylene can be replaced by oxygen;

$R^{17}$ is $C_1$-$C_4$-alkyl; $C_1$-$C_4$-haloalkyl;

$R^{18}$ is $C_1$-$C_4$-alkyl; N,N-dimethylamino;

$R^{19}$ is $C_1$-$C_4$-alkyl; $C_1$-$C_4$-haloalkyl; $C_2$-$C_4$-alkoxyalkyl; $C_3$-$C_4$-alkenyl; $C_3$-$C_4$-alkynyl; $C_3$-$C_4$-haloalkenyl; phenyl; phenyl substituted by fluorine, chlorine, bromine, methyl or methoxy;

n is 1 or 2;

$R^{20}$ is hydrogen or $C_1$-$C_4$-alkyl;

$R^{21}$ is $R^{12}$; phenyl or benzyl, each of which is unsubstituted or substituted by at least one of the following: one to five halogens, or one to three of the following: cyano, nitro, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio or $C_1$-$C_4$-haloalkylthio;

and the environmentally compatible salts thereof.

2. A compound of the formula I as claimed in claim 1 or the environmentally compatible salts thereof, where A is (A1) or (A9), W is oxygen and $R^4$ is hydrogen.

3. A compound of the formula I as claimed in claim 1 or the environmentally compatible salts thereof, where
A is (A1) or (A9),
W is oxygen and
$R^4$ is hydrogen.

4. A herbicide containing an effective amount of a sulfonamide of the formula I as claimed in claim 1 or the salt thereof in addition to conventional herbicidal carriers.

5. A herbicide containing an effective amount of a sulfonamide of the formula I as claimed in claim 1, where
A is a radical of the formula (A1),
W is oxygen, and
$R^4$ is hydrogen,
or a salt thereof, and conventional herbicidal carriers.

6. An agent for influencing plant growth, containing an effective amount of a sulfonamide of the formula I as claimed in claim 1 or the salt thereof in addition to conventional inert additives.

7. A process for controlling undesired plant growth, which comprises allowing a sulfonamide of the formula I:

$$A-SO_2-N(H)-\overset{\overset{W}{\|}}{C}-B \qquad (I)$$

where
A is

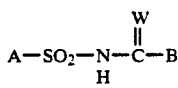
(A1)

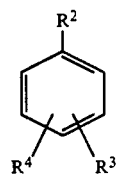
(A9)

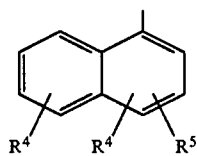
(A10)

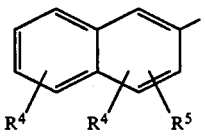

W is oxygen or sulfur;
B is 3-, 4- or 5-pyrazolyl, disubstituted on carbon by $R^8$ and monosubstituted on nitrogen by $R^9$;
$R^2$ is halogen; cyano; thiocyano;
$C_1-C_6$-alkyl which is unsubstituted or substituted by at least one of the following: one to five halogens, or one of the following: $C_1-C_4$-alkoxy, $C_1-C_4$-haloalkoxy, $C_1-C_4$-alkylthio, $C_1-C_4$-haloalkylthio, phenyl, phenoxy or phenylthio, where each of the phenyls is unsubstituted or substituted by at least one of the following: one to five halogens, or one to three of the following: $C_1-C_4$-alkyl, $C_1-C_4$-haloalkyl, $C_1-C_4$-alkoxy, $C_1-C_4$-haloalkoxy, $C_1-C_4$-alkylthio or $C_1-C_4$-haloalkylthio; $C_3-C_6$-cycloalkyl, $C_3-C_8$-cycloalkoxy, $C_3-C_6$-cycloalkylthio, $C_5-C_6$-cycloalkenyl, $C_5-C_8$-cycloalkenyloxy or $C_5-C_8$-cycloalkenylthio, each of which is unsubstituted or substituted by at least one of the following: one to five halogens, or one to three of the following: $C_1-C_4$-alkyl, $C_1-C_4$-haloalkyl, $C_1-C_4$-alkoxy, $C_1-C_4$-haloalkoxy, $C_1-C_4$-alkylthio or $C_1-C_4$-haloalkylthio;
phenyl, phenoxy, benzyloxy or benzylthio, each of which is unsubstituted or substituted by at least one of the following: one to five halogens, or one to three of the following: cyano, nitro, $C_1-C_4$-alkyl, $C_1-C_4$-haloalkyl, $C_1-C_4$-alkoxy, haloalkoxy, $C_1-C_4$-alkylthio or $C_1-C_4$-haloalkylthio;
saturated, or unsaturated 5-7-membered heterocycle, said unsaturated 5-7 membered heterocycle having one or two double bonds, said saturated or unsaturated 5-7 membered heterocycle having one or two heteroatoms selected from nitrogen, oxygen and sulfur and which is unsubstituted or substituted by one or two of the following: halogen, cyano, nitro, $C_1-C_4$-alkyl, $C_1-C_4$-alkoxy, $C_1-C_4$-alkylthio, $C_1-C_4$-haloalkyl, $C_1-C_4$-haloalkoxy or $C_1-C_4$-haloalkylthio;
$C_1-C_4$-alkoxy or $C_1-C_4$-alkylthio, $C_2-C_6$-alkenyl or $C_2-C_6$-alkenyloxy or $C_2-C_6$-alkenylthio, $C_2-C_6$-alkynyl, $C_2-C_6$-alkynyloxy or $C_2-C_6$-alkynylthio, where the said alkoxy, alkylthio, alkenyl, alkynyl, alkenyloxy(thio) and alkynyloxy(thio) is unsubstituted or substituted by at least one of the following: one to five halogens, or one of the following: $C_1-C_4$-alkoxy, $C_1-C_4$-haloalkoxy, $C_1-C_4$-alkylthio, $C_1-C_4$-haloalkylthio; phenyl, phenoxy, phenylthio, benzyloxy or benzylthio; $COR^{12}$; $COQR^{13}$; $SO_2NR^{15}R^{16}$; $SO_2OR^{17}$; $OSO_2R^{18}$; $S(O)_nR^{19}$;
$R^3$ is $R^6$; $COQR^{13}$; $SO_2NR^{15}R^{16}$; $SO_2OR^{17}$; $OSO_2R^{18}$; $S(O)_nR^{19}$;
$R^4$ is hydrogen; halogen; cyano;
$C_1-C_4$-alkyl or $C_1-C_4$-alkyl substituted by one to five halogens; $C_1-C_4$-alkoxy; $C_1-C_4$-haloalkoxy; $C_1-C_4$-alkylthio; $C_1-C_4$-haloalkylthio;
$R^5$ is hydrogen; nitro or $R^2$;
$R^6$ is hydrogen; halogen; cyano;
$C_1-C_4$-alkyl, $C_1-C_4$-alkyl substituted by at least one of the following: one to five halogens, or one of the following: $C_1-C_4$-alkoxy, $C_1-C_4$-haloalkoxy, $C_1-C_4$-alkylthio, $C_1-C_4$-haloalkylthio, OH, SH or cyano;
$C_1-C_4$-alkoxy, $C_1-C_4$-alkylthio, $C_1-C_4$-haloalkoxy or $C_1-C_4$-haloalkylthio, each of which is unsubstituted or substituted by the following: $C_1-C_4$-alkoxy, $C_1-C_4$-haloalkoxy, $C_1-C_4$-alkylthio or $C_1-C_4$-haloalkylthio;
$R^8$ is hydrogen; nitro; or $R^2$, or two vicinal $R^2$ together form a $C_3$ chain or a $C_4-C_6$ chain unsubstituted or in which one methylene is replaced by oxygen or $C_1-C_4$-alkylimino;
$R^9$ is hydrogen;
$C_1-C_6$-alkyl which is unsubstituted or substituted by at least one of the following: one to five halogens, or one of the following: $C_1-C_4$-alkoxy; $C_1-C_4$-haloalkoxy; $C_1-C_4$-alkylthio; $C_1-C_4$-haloalkylthio, phenyl, phenoxy or phenylthio, wherein cyclic groups are unsubstituted or substituted by at least one of the following: one to five halogens, or one to three of the following: cyano, $C_1-C_4$-alkyl, $C_1-C_4$-haloalkyl, $C_1-C_4$-alkoxy, $C_1-C_4$-haloalkoxy, $C_1-C_4$-alkylthio or $C_1-C_4$-haloalkylthio; $C_3-C_6$- cycloalkyl or $C_5$–$C_6$-cycloalkenyl, each of which is unsubstituted or substituted by at least one of the following: one to five halogens, or one to three of the following: $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio, or $C_1$–$C_4$-haloalkylthio;

phenyl which is unsubstituted or substituted by at least one of the following: one to five halogens, or one to three of the following: cyano, nitro, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio or $C_1$–$C_4$-haloalkylthio;

$C_2$–$C_6$-alkenyl or $C_2$–$C_6$-alkynyl, each of which is unsubstituted or substituted by at least one of the following: one to five halogens, or one of the following: $C_1$–$C_4$-alkoxy, $C_1$–$C_4$-haloalkoxy, $C_1$–$C_4$-alkylthio or $C_1$–$C_4$-haloalkylthio, phenyl, phenoxy, phenylthio, benzyloxy or benzylthio; $COR^{21}$;

$R^{10}$ is phenyl, benzyl, phenoxy, benzyloxy, phenylthio or benzylthio, each of which is unsubstituted or substituted by at least one of the following: one to five halogens, or one to three of the following: cyano, nitro, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio or $C_1$–$C_4$-haloalkylthio;

$R^{11}$ is hydrogen; phenyl or benzyl, each of which is unsubstituted or substituted by at least one of the following: one to five halogens, or one to three of the following: cyano, nitro, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio or $C_1$–$C_4$-haloalkylthio;

$R^{12}$ is $C_1$–$C_4$-alkyl which is unsubstituted or substituted by halogen or methoxy; $C_3$–$C_5$-cycloalkyl which is unsubstituted or substituted by chlorine or fluorine; $C_3$–$C_4$-alkenyl;

Q is oxygen or $NR^{14}$;

$R^{13}$ is hydrogen;

$C_1$–$C_6$-alkyl, $C_1$–$C_6$-alkyl substituted by one to three of the following: halogen, $C_1$–$C_4$-alkoxy, $C_1$–$C_4$-alkylthio, $C_1$–$C_4$-haloalkoxy, $C_1$–$C_4$-alkoxy-$C_1$–$C_2$-alkoxy, $C_3$–$C_6$-cycloalkyl, or phenyl;

$C_3$–$C_6$-cycloalkyl, which is substituted one to three times by $C_1$–$C_4$-alkyl; $C_3$–$C_6$-alkenyl; $C_3$–$C_6$-alkynyl; phenyl, phenyl substituted by at least one of the following: one to five halogens, or one to three of the following: cyano, nitro, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio or $C_1$–$C_4$-haloalkylthio;

$R^{14}$ is $OR^{20}$; $R^{13}$ or forms together with another $R^{13}$ a $C_4$–$C_6$-alkylene chain or a $C_4$–$C_6$-alkylene chain in which one methylene is replaced by oxygen or $C_1$–$C_4$-alkylimino;

$R^{15}$ is $C_1$–$C_4$-alkyl; $C_3$–$C_4$-alkenyl; $C_3$–$C_4$-alkynyl; cyclopropylmethyl; $C_3$–$C_4$-cycloalkyl;

$R^{16}$ is hydrogen; $C_1$–$C_4$-alkyl; $C_3$–$C_4$-alkenyl; or forms together with $R^{15}$ a $C_4$–$C_6$-alkylene chain in which one methylene can be replaced by oxygen;

$R^{17}$ is $C_1$–$C_4$-alkyl; $C_1$–$C_4$-haloalkyl;

$R^{18}$ is $C_1$–$C_4$-alkyl; N,N-dimethylamino;

$R^{19}$ is $C_1$–$C_4$-alkyl; $C_1$–$C_4$-haloalkyl; $C_2$–$C_4$-alkoxyalkyl; $C_3$–$C_4$-alkenyl; $C_3$–$C_4$-alkynyl; $C_3$–$C_4$-haloalkenyl; phenyl; phenyl substituted by fluorine, chlorine, bromine, methyl or methoxy;

n is 1 or 2;

$R^{20}$ is hydrogen or $C_1$–$C_4$-alkyl;

$R^{21}$ is $R^{12}$; phenyl or benzyl, each of which is unsubstituted or substituted by at least one of the following: one to five halogens, or one to three of the following: cyano, nitro, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio or $C_1$–$C_4$-haloalkylthio; or the salt thereof to act on plants or their habitat.

8. A process for influencing plant growth, which comprises allowing a sulfonamide of the formula I:

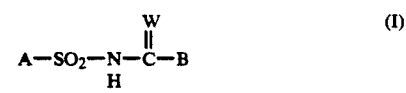

where A is

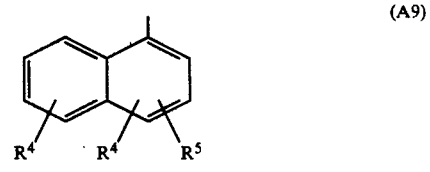

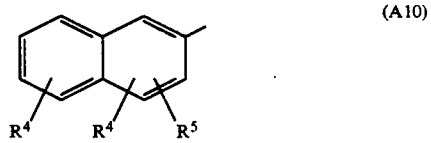

W is oxygen or sulfur;

B is 3-, 4- or 5-pyrazolyl, disubstituted on carbon by $R^8$ and monosubstituted on nitrogen by $R^9$;

$R^2$ is halogen; cyano; thiocyano;

$C_1$–$C_6$-alkyl which is unsubstituted or substituted by at least one of the following: one to five halogens, or one of the following: $C_1$–$C_4$-alkoxy, $C_1$–$C_4$-haloalkoxy, $C_1$–$C_4$-alkylthio, $C_1$–$C_4$-haloalkylthio, phenyl, phenoxy or phenylthio, where each of the phenyls is unsubstituted or substituted by at least one of the following: one to five halogens, or one to three of the following: $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio or $C_1$–$C_4$-haloalkylthio; $C_3$–$C_6$-cycloalkyl, $C_3$–$C_8$-cycloalkoxy, $C_3$–$C_6$-cycloalkylthio, $C_5$–$C_6$-cycloalkenyl, $C_5$–$C_8$-cycloalkenyloxy or $C_5$–$C_8$-cycloalkenylthio, each of which is unsubstituted or substituted by at least one of the following: one to five halogens, or one to three of the following: $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio or $C_1$–$C_4$-haloalkylthio; phenyl, phenoxy, benzyloxy or benzylthio, each of which is unsubstituted or substituted by at least one of the following: one to five halogens, or one to three of the following: cyano, nitro, $C_1$–$C_4$-alkyl, $C_1$–$C_4$-haloalkyl, $C_1$–$C_4$-alkoxy, haloalkoxy, $C_1$–$C_4$-alkylthio or $C_1$–$C_4$-haloalkylthio; saturated, or unsaturated 5-7-membered heterocycle, said unsaturated 5-7 membered heterocycle having one or two double bonds, said saturated or unsaturated 5-7 membered heterocycle having one or two heteroatoms selected from nitrogen, oxygen and sulfur and which is unsubstituted or substituted by one or two of the following: halogen, cyano, nitro, $C_1$–$C_4$-alkyl, $C_1$–$C_4$-alkoxy, $C_1$–$C_4$-alkylthio, $C_1$–$C_4$-haloalkyl, $C_1$–$C_4$-haloalkoxy or $C_1$–$C_4$-haloalkylthio; $C_1$–$C_4$-alkoxy or $C_1$–$C_4$-alkylthio, $C_2$–$C_6$-alkenyl or $C_2$–$C_6$-alkenyloxy or $C_2$–$C_6$-alkenylthio, $C_2$–$C_6$-alkynyl, $C_2$–$C_6$-alkynyloxy or $C_2$–$C_6$-alkynylthio, where the said alkoxy, alkylthio, alkenyl, alkynyl, alkenyloxy(thio) and alkynyloxy(thio) is unsubstituted or substituted by at least one of the following: one to five halogens, or one of the following: $C_1$–$C_4$-alkoxy, $C_1$–$C_4$-haloalkoxy, $C_1$–$C_4$-alkylthio, $C_1$–$C_4$-haloalkylthio; phenyl, phenoxy, phenylthio, benzyloxy or benzylthio; $COR^{12}$; $COQR^{13}$; $SO_2NR^{15}R^{16}$; $SO_2OR^{17}$; $OSO_2R^{18}$; $S(O)_nR^{19}$;

$R^3$ is $R^6$; $COQR^{13}$; $SO_2NR^{15}R^{16}$; $SO_2OR^{17}$; $OSO_2R^{18}$; $S(O)_nR^{19}$;

$R^4$ is hydrogen; halogen; cyano; $C_1$–$C_4$-alkyl or $C_1$–$C_4$-alkyl substituted by one to five halogens; $C_1$–$C_4$-alkoxy; $C_1$–$C_4$-haloalkoxy; $C_1$–$C_4$-alkylthio; $C_1$–$C_4$-haloalkylthio;

$R^5$ is hydrogen; nitro or $R^2$;

$R^6$ is hydrogen; halogen; cyano;
$C_1$–$C_4$-alkyl, $C_1$–$C_4$-alkyl substituted by at least one of the following: one to five halogens, or one of the following: $C_1$–$C_4$-alkoxy, $C_1$–$C_4$-haloalkoxy, $C_1$–$C_4$-alkylthio, $C_1$–$C_4$-haloalkylthio, OH, SH or cyano; $C_1$–$C_4$-alkoxy, $C_1$–$C_4$-alkylthio, $C_1$–$C_4$-haloalkoxy or $C_1$–$C_4$-haloalkylthio, each of which is unsubstituted or substituted by the following: $C_1$–$C_4$-alkoxy, $C_1$–$C_4$-haloalkoxy, $C_1$–$C_4$-alkylthio or $C_1$–$C_4$-haloalkylthio;

$R^8$ is hydrogen; nitro; or $R^2$, or two vicinal $R^2$ together form a $C_3$ chain or a $C_4$–$C_6$ chain unsubstituted or in which one methylene is replaced by oxygen or $C_1$–$C_4$-alkylimino;

$R^9$ is hydrogen; $C_1$–$C_6$-alkyl which is unsubstituted or substituted by at least one of the following: one to five halogens, or one of the following: $C_1$–$C_4$-alkoxy; $C_1$–$C_4$-haloalkoxy; $C_1$–$C_4$-alkylthio; $C_1$–$C_4$-haloalkylthio, phenyl, phenoxy or phenylthio, wherein cyclic groups are unsubstituted or substituted by at least one of the following: one to five halogens, or one to three of the following: cyano, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio or $C_1$–$C_4$-haloalkylthio; $C_3$–$C_6$-cycloalkyl or $C_5$–$C_6$-cycloalkenyl, each of which is unsubstituted or substituted by at least one of the following: one to five halogens, or one to three of the following: $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio, or $C_1$–$C_4$-haloalkylthio;
phenyl which is unsubstituted or substituted by at least one of the following: one to five halogens, or one to three of the following: cyano, nitro, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio or $C_1$–$C_4$-haloalkylthio; $C_2$–$C_6$-alkenyl or $C_2$–$C_6$-alkynyl, each of which is unsubstituted or substituted by at least one of the following: one to five halogens, or one of the following: $C_1$–$C_4$-alkoxy, $C_1$–$C_4$-haloalkoxy, $C_1$–$C_4$-alkylthio or $C_1$–$C_4$-haloalkylthio, phenyl, phenoxy, phenylthio, benzyloxy or benzylthio; $COR^{21}$;

$R^{10}$ is phenyl, benzyl, phenoxy, benzyloxy, phenylthio or benzylthio, each of which is unsubstituted or substituted by at least one of the following: one to five halogens, or one to three of the following: cyano, nitro, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio or $C_1$–$C_4$-haloalkylthio;

$R^{11}$ is hydrogen; phenyl or benzyl, each of which is unsubstituted or substituted by at least one of the following: one to five halogens, or one to three of the following: cyano, nitro, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio or $C_1$–$C_4$-haloalkylthio;

$R^{12}$ is $C_1$–$C_4$-alkyl which is unsubstituted or substituted by halogen or methoxy; $C_3$–$C_5$-cycloalkyl which is unsubstituted or substituted by chlorine or fluorine; $C_3$–$C_4$-alkenyl;

Q is oxygen or $NR^{14}$;

$R^{13}$ is hydrogen; $C_1$–$C_6$-alkyl, $C_1$–$C_6$-alkyl substituted by one to three of the following: halogen, $C_1$–$C_4$-alkoxy, $C_1$–$C_4$-alkylthio, $C_1$–$C_4$-haloalkoxy, $C_1$–$C_4$-alkoxy-$C_1$–$C_2$-alkoxy, $C_3$–$C_6$-cycloalkyl, or phenyl;
$C_3$–$C_6$-cycloalkyl, which is substituted one to three times by $C_1$–$C_4$-alkyl; $C_3$–$C_6$-alkenyl; $C_3$–$C_6$-alkynyl; phenyl, phenyl substituted by at least one of the following: one to five halogens, or one to three of the following: cyano, nitro, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio or $C_1$–$C_4$-haloalkylthio;

$R^{14}$ is $OR^{20}$; $R^{13}$ or forms together with another $R^{13}$ a $C_4$–$C_6$-alkylene chain or a $C_4$–$C_6$-alkylene chain in which one methylene is replaced by oxygen or $C_1$–$C_4$-alkylimino;

$R^{15}$ is $C_1$–$C_4$-alkyl; $C_3$–$C_4$-alkenyl; $C_3$–$C_4$-alkynyl; cyclopropylmethyl; $C_3$–$C_4$-cycloalkyl;

$R^{16}$ is hydrogen; $C_1$–$C_4$-alkyl; $C_3$–$C_4$-alkenyl; or forms together with $R^{15}$ a $C_4$–$C_6$-alkylene chain in which one methylene can be replaced by oxygen;

$R^{17}$ is $C_1$–$C_4$-alkyl; $C_1$–$C_4$-haloalkyl;

$R^{18}$ is $C_1$–$C_4$-alkyl; N,N-dimethylamino;

$R^{19}$ is $C_1$–$C_4$-alkyl; $C_1$–$C_4$-haloalkyl; $C_2$–$C_4$-alkoxyalkyl; $C_3$–$C_4$-alkenyl; $C_3$–$C_4$-alkynyl; $C_3$–$C_4$-haloalkenyl; phenyl; phenyl substituted by fluorine, chlorine, bromine, methyl or methoxy;

n is 1 or 2;

$R^{20}$ is hydrogen or $C_1$–$C_4$-alkyl;

$R^{21}$ is $R^{12}$; phenyl or benzyl, each of which is unsubstituted or substituted by at least one of the following: one to five halogens, or one to three of the following: cyano, nitro, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio or $C_1$–$C_4$-haloalkylthio; or the salt thereof to act on plants or their habitat.

* * * * *